US007956894B2

(12) United States Patent
Akers et al.

(10) Patent No.: US 7,956,894 B2
(45) Date of Patent: *Jun. 7, 2011

(54) APPARATUS AND METHOD FOR COMPUTERIZED MULTI-MEDIA MEDICAL AND PHARMACEUTICAL DATA ORGANIZATION AND TRANSMISSION

(75) Inventors: William Rex Akers, Colleyville, TX (US); Jeff W. Canterbury, Fort Worth, TX (US); Blake B. Miller, Austin, TX (US); Craig Alan Walker, Austin, TX (US); James R. King, Waxahachie, TX (US); Jerry L. Graves, Benbrook, TX (US); Jay Travis Patterson, Arlington, TX (US); Robert J. Normyle, Colleyville, TX (US); Kevin P. Hale, Fort Worth, TX (US); Brandon T. Watts, Park City, UT (US); Karen D. Rau, Farwell, MN (US); Deborah L. Jenkins, Fort Worth, TX (US)

(73) Assignee: William Rex Akers, Fort Worth, TX (US)

( * ) Notice: Subject to any disclaimer, the term of this patent is extended or adjusted under 35 U.S.C. 154(b) by 1294 days.

This patent is subject to a terminal disclaimer.

(21) Appl. No.: 10/369,843

(22) Filed: Feb. 19, 2003
(Under 37 CFR 1.47)

(65) Prior Publication Data

US 2004/0017475 A1 Jan. 29, 2004

Related U.S. Application Data

(63) Continuation-in-part of application No. 09/170,509, filed on Oct. 13, 1998, now Pat. No. 6,597,392, and a continuation-in-part of application No. 09/851,745, filed on May 9, 2001.

(60) Provisional application No. 60/061,761, filed on Oct. 14, 1997.

(51) Int. Cl.
*H04N 5/225* (2006.01)
*H04N 7/00* (2006.01)
*H04N 11/00* (2006.01)
*G06Q 10/00* (2006.01)
*G06Q 50/00* (2006.01)
*A61B 5/00* (2006.01)

(52) U.S. Cl. .................. 348/207.1; 348/552; 348/231.2; 348/333.02; 705/2; 600/301

(58) Field of Classification Search ............... 348/207.1, 348/77; 600/301
See application file for complete search history.

(56) References Cited

U.S. PATENT DOCUMENTS 5,072,383 A 12/1991 Brimm et al.
(Continued)

FOREIGN PATENT DOCUMENTS

WO WO 00/16222 A1 3/2000

OTHER PUBLICATIONS

Search Report for PCT/US02/14682 Dated Dec. 27, 2002 in related PCT filing of pending U.S. Appl. No. 09/851,745.
(Continued)

*Primary Examiner* — Kelly L Jerabek
(74) *Attorney, Agent, or Firm* — Carr LLP

(57) ABSTRACT

An apparatus for multi-media data organization and transmission is provided. The apparatus has a computer having a microprocessor, a memory storage, a display for providing information to a user, and an input device. An image-recording device is electrically-coupled to the computer for capturing images for storage in the memory storage of the computer. A database, which has a structure defined in the memory storage, receives and stores a plurality of information relating to an event. A program, being executable by the computer, provides a graphical user interface on the display. The program has an imaging module with document and image capture filing and scanning functions. The graphical user interface receives an input from the input device and from the image-recording device. In a further aspect of the invention, the program has a communications module for transmission of the plurality of information relating to the event to a remote location.

68 Claims, 12 Drawing Sheets

U.S. PATENT DOCUMENTS

| | | | |
|---|---|---|---|
| 5,262,944 A | 11/1993 | Weisner et al. | |
| 5,553,609 A | 9/1996 | Chen et al. | |
| 5,592,664 A | 1/1997 | Starkey | |
| 5,597,995 A * | 1/1997 | Williams et al. | 235/375 |
| 5,810,747 A | 9/1998 | Brudny et al. | |
| 5,832,449 A | 11/1998 | Cunningham | 705/3 |
| 5,842,175 A | 11/1998 | Andros et al. | |
| 5,845,255 A | 12/1998 | Mayaud | 705/3 |
| 5,867,821 A | 2/1999 | Ballantyne et al. | 705/2 |
| 5,899,998 A | 5/1999 | McGauley et al. | 707/104 |
| 5,903,889 A | 5/1999 | de la Huerga et al. | |
| 5,907,493 A | 5/1999 | Boyer et al. | 364/479.01 |
| 5,924,074 A | 7/1999 | Evans | 705/3 |
| 5,950,630 A | 9/1999 | Portwood et al. | 128/897 |
| 5,987,519 A | 11/1999 | Peifer | 709/230 |
| 6,006,191 A | 12/1999 | DiRienzo | 705/2 |
| 6,021,393 A | 2/2000 | Honda et al. | |
| 6,031,572 A | 2/2000 | Christopoulos | 348/397 |
| 6,031,929 A | 2/2000 | Maitz et al. | 382/132 |
| 6,035,323 A | 3/2000 | Narayen et al. | |
| 6,038,465 A | 3/2000 | Melton, Jr. | 600/407 |
| 6,047,259 A | 4/2000 | Campbell et al. | |
| 6,055,506 A | 4/2000 | Frasca, Jr. | 705/3 |
| 6,055,507 A | 4/2000 | Cunningham | 705/3 |
| 6,067,524 A | 5/2000 | Byerly et al. | 705/3 |
| 6,125,350 A | 9/2000 | Dirbas | |
| 6,131,090 A | 10/2000 | Basso, Jr. et al. | 706/23 |
| 6,157,935 A | 12/2000 | Tran et al. | |
| 6,202,923 B1 * | 3/2001 | Boyer et al. | 235/375 |
| 6,219,587 B1 | 4/2001 | Ahlin et al. | 700/233 |
| 6,234,964 B1 | 5/2001 | Iliff | |
| 6,263,330 B1 | 7/2001 | Bessette | 707/4 |
| 6,272,470 B1 | 8/2001 | Teshima | |
| 6,305,377 B1 | 10/2001 | Portwood et al. | 128/897 |
| 6,370,841 B1 | 4/2002 | Chudy et al. | 53/411 |
| 6,597,392 B1 | 7/2003 | Jenkins et al. | |
| 7,027,872 B2 | 4/2006 | Thompson | |
| 7,039,810 B1 | 5/2006 | Nichols | |
| 7,249,036 B2 | 7/2007 | Bayne | |
| 7,251,610 B2 | 7/2007 | Alban et al. | |
| 2002/0169637 A1* | 11/2002 | Akers et al. | 705/3 |

OTHER PUBLICATIONS

Gomez, E. J. et al: "A Broadband Multimedia Collaborative System for Advanced Teleradiology and Medical Imaging Diagnosis"; IEEE Transactions on Information Technology in Biomedicine, IEEE Service Center, Los Alamitos, CA, USA, vol. 2, No. 3, Sep. 1998, pp. 146-155; XP-000831159.
Gomez, E.J. et al: "Optimisation and Evaluation of an Asynchronous Transfer Mode Teleradiology Co-operative System: the Experience of Emerald and the Bonaparte Projects"; Computer Methods and Programs in Biomedicine, Elsevier, Ireland, vol. 64, No. 3, Mar. 2001, pp. 201-214; XP-002389681.
European Patent Office: Supplementary European Search Report; EP Application No. 02_74_7825; Munich DE, Aug. 8, 2006.
U.S. Appl. No. 10/366,179; Office Action; Mar. 31, 2006.
U.S. Appl. No. 10/366,179; Response to Office Action; Oct. 2, 2006.
U.S. Appl. No. 10/366,179; Final Office Action; Feb. 20, 2007.
U.S. Appl. No. 10/366,179; Response to Office Action; Jun. 20, 2007.
U.S. Appl. No. 10/366,179; Advisory Action; Jun. 26, 2007.
U.S. Appl. No. 10/366,179; Office Action; Jul. 31, 2007.
U.S. Appl. No. 10/366,179; Response to Office Action; Feb. 4, 2008.
U.S. Appl. No. 10/366,179; Final Office Action; Apr. 22, 2008.
U.S. Appl. No. 10/366,179; Response to Office Action; Jun. 30, 2008.
U.S. Appl. No. 10/366,179; Advisory Action; Jul. 16, 2008.
U.S. Appl. No. 10/366,179; Office Action; Oct. 28, 2008.
U.S. Appl. No. 09/170,509; Office Action; Jun. 19, 2002.
U.S. Appl. No. 09/170,509; Response to Office Action; Sep. 17, 2002.
U.S. Appl. No. 09/170,509; Notice of Allowance/Notice of Allowability; Dec. 3, 2002.
U.S. Appl. No. 10/366,179: Final Office Action; Jul. 31, 2009.
U.S. Appl. No. 09/851,745; Petition and IDS; Oct. 9, 2001.
U.S. Appl. No. 09/851,745; Decision on Petition; Dec. 27, 2001.
U.S. Appl. No. 09/851,745; Petition; Jan. 17, 2002.
U.S. Appl. No. 09/851,745; Decision on Petition; Jan. 18, 2002.
U.S. Appl. No. 09/851,745; Office Action; Sep. 12, 2002.
U.S. Appl. No. 09/851,745; Response; Oct. 9, 2002.
U.S. Appl. No. 09/851,745; Final Office Action; Jan. 2, 2003.
U.S. Appl. No. 09/851,745; Examiner's Interview Summary; Jan. 21, 2003.
U.S. Appl. No. 09/851,745; Response; Mar. 11, 2003.
U.S. Appl. No. 09/851,745; Advisory Action; Mar. 21, 2003.
U.S. Appl. No. 09/851,745; Appeal Brief; Jul. 11, 2003.
U.S. Appl. No. 09/851,745; Examiner's Answer; Mar. 9, 2004.
U.S. Appl. No. 09/851,745; Reply Brief; May 13, 2004.
U.S. Appl. No. 09/851,745; Order Returning Undocketed Appeal to Examiner; Aug. 23, 2005.
U.S. Appl. No. 09/851,745; Second Examiner's Answer; Mar. 7, 2006.
U.S. Appl. No. 09/851,745; Final Office Action; Jan. 9, 2007.
U.S. Appl. No. 09/851,745; Office Action May 22, 2007.
U.S. Appl. No. 09/851,745; Response; Aug. 22, 2007.
U.S. Appl. No. 09/851,745; Final Office Action Nov. 19, 2007.
U.S. Appl. No. 09/851,745; Response; Apr. 21, 2008.
U.S. Appl. No. 09/851,745; Office Action; Jul. 24, 2008.
U.S. Appl. No. 09/851,745; Response; Nov. 24, 2008.
U.S. Appl. No. 09/851,745; Final Office Action; Mar. 4, 2009.
U.S. Appl. No. 10/366,179; Response; Apr. 28, 2009.
U.S. Appl. No. 10/366,179; Response; Feb. 1, 2010.
U.S. Appl. No. 10/366,179; Office Action; Aug. 16, 2010.
U.S. Appl. No. 09/851,745; Response; Jul. 6, 2009.
U.S. Appl. No. 09/851,745; Advisory Action; Jul. 23, 2009.
U.S. Appl. No. 09/851,745; RCE/IDS; Jul. 28, 2009.
U.S. Appl. No. 09/851,745; Office Action; Dec. 10, 2009.
U.S. Appl. No. 09/851,745; Examiner's Interview Summary; Jun. 10, 2010.
U.S. Appl. No. 09/851,745; Response; Jun. 10, 2010.
U.S. Appl. No. 09/851,745; Notice of Allowance; Sep. 24, 2010.
U.S. Appl. No. 09/851,745; Amendment After Allowance; Dec. 23, 2010.
Smith, Kevin L.; Statement of Facts in Support of Filing on Behalf of Non-signing Inventor; U.S. Appl. No. 09/170,509; Jan. 19, 1999.
Smith, Kevin L.; Letter to Deborah Jenkins; Oct. 22, 1998.
Smith, Kevin L.; Letter to Deborah Jenkins; Nov. 4, 1998.
Jenkins, Deborah L; Letter to Kevin L. Smith; Nov. 12, 1998.
Smith, Kevin L.; Letter to Deborah Jenkins; Nov. 25, 1998.
Smith, Kevin L.; Letter to Deborah Jenkins; Dec. 17, 1998.
Jenkins, Deborah L.; Letter to Kevin L. Smith; Dec. 21, 1998.
Smith, Kevin L.; Letter to Deborah Jenkins; Dec. 22, 1998.
Jenkins, Deborah L.; Letter to Kevin L. Smith; Dec. 22, 1998.
Jenkins, Deborah L.; Declaration in U.S. Appl. No. 09/170,509; Dec. 24, 1998.
Akers, Wm. Rex; Statement Establishing Proprietary Interest in U.S. Appl. No. 09/170,509; Jan. 19, 1999.
Akers, Wm. Rex; Added Page To Declaration by Person with Sufficient Proprietary Interest U.S. Appl. No. 09/170,509; Jan. 19, 1999.
Stewart et al., "DICOM image integration into an electronic medical record using thin viewing clients"; Proceedings of the SPIE—The International Society for Optical Engineering, vol. 3339, Feb. 24-26, 1998, pp. 322-328.

* cited by examiner

APPARATUS AND METHOD FOR COMPUTERIZED MULTI-MEDIA MEDICAL AND PHARMACEUTICAL DATA ORGANIZATION AND TRANSMISSION

CROSS-REFERENCE TO RELATED APPLICATIONS

This application claims the benefit of U.S. Provisional Application Ser. No. 60/061,761, filed Oct. 14, 1997; U.S. patent application Ser. No. 09/170,509, filed Oct. 13, 1998, and U.S. patent application Ser. No. 09/851,745, filed May 5, 2001, each of which are hereby incorporated herein by reference for all purposes.

TECHNICAL FIELD

The present invention relates to a computer-implemented diagnostic imaging tool for capturing multi-media data for organization and transmission from a database, and in particular to a telemedicine technique using multi-media data capture, storage, and transmission of episodes-of-care for medical consultation.

BACKGROUND OF THE INVENTION

In remote areas of the world, or with infirm patients unable to travel to hospitals, telecommunications have historically been used to attempt diagnosis over distances. In the beginning, voice conversations were held with physicians in an effort to diagnose a patient over a distance. But the diagnosis was often unreliable because the examining physician was unable to view the patient and their symptoms first-hand, leaving the accuracy of the diagnosis to the capability of the caregiver with the patient to relay the information with sufficient information for a diagnosis.

Improvements had been made with the use of image transfers over telecommunications lines. The images of the affected region—such as ulcers, lesions, or the like—could be electronically transmitted to a physician for review. But this method had limitations due to the inaccuracy of time records to track development of a condition.

Also, image files would have haphazard naming conventions that failed to convey any meaning to those unfamiliar with the naming conventions of the primary medical provider. Another limitations of remote patient care devices has been the user acceptance to deploy the technology in the marketplace.

Thus, a need exists for an inexpensive device for capturing multi-media data for organization and transmission from a database that is portable with the medical community. Further, a need exists for a high-definition capture device to provide high-definition images for analysis. Also, a need exists for arranging the high-definition images, with pertinent date-time information, in an orderly manner that is readily accessible by a user.

BRIEF SUMMARY OF THE INVENTION

Accordingly, an apparatus for multi-media data organization and transmission is provided in one exemplary embodiment of the invention. The apparatus has a computer having a microprocessor, a memory storage, a display for providing information to a user, and an input device. An image-recording device is electrically-coupled to the computer for capturing images for storage in the memory storage of the computer. A database, which has a structure defined in the memory storage, receives and stores a plurality of information relating to an event. A program, being executable by the computer, provides a graphical user interface on the display. The program has an imaging module with document and image capture filing and scanning functions. The graphical user interface receives an input from the input device and from the image-recording device. In a further aspect of the invention, the program has a communications module for transmission of the plurality of information relating to the event to a remote location.

The foregoing has outlined rather broadly the features and technical advantages of an exemplary embodiment of the present invention in order that the detailed description of exemplary embodiments of the invention that follows may be better understood. Additional features and advantages of embodiments of the invention will be described hereinafter.

BRIEF DESCRIPTION OF THE SEVERAL VIEWS OF THE DRAWINGS

For a more complete understanding of the present invention, and the advantages thereof, reference is now made to the following description of exemplary embodiments taken in conjunction with the accompanying drawings, in which.

DETAILED DESCRIPTION OF THE INVENTION

Figure 1:
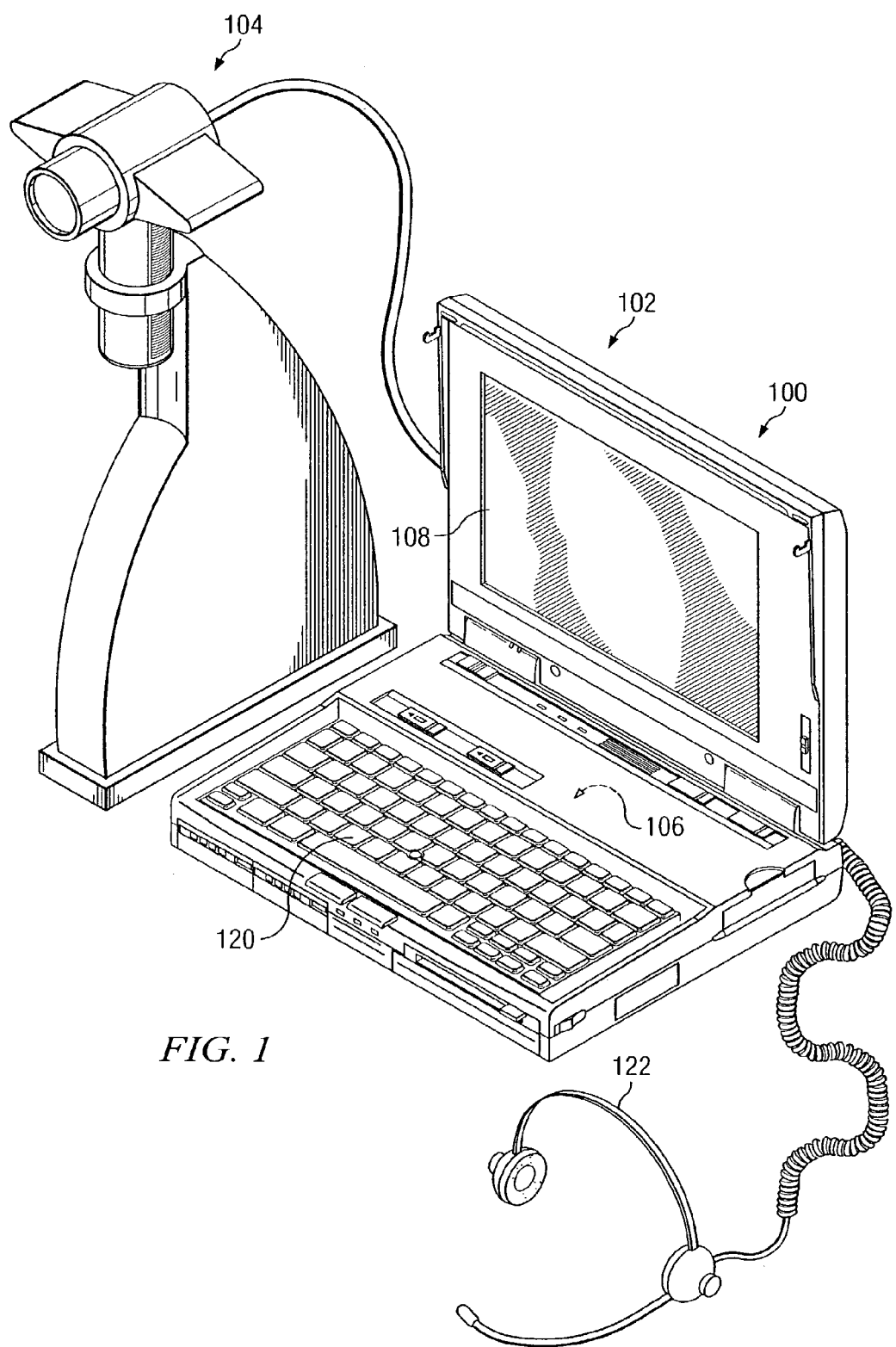
FIG. 1 is an illustration of an exemplary capture-and-storage device for providing health care access to remote and rural patients with image-assisted diagnosis.

In the following description, numerous specific details are set forth to provide a thorough understanding of the present invention. It should be noted, however, that those skilled in the art are capable of practicing the present invention without such specific details. Referring to the drawings, depicted elements are not necessarily shown to scale, and like or similar elements are designated by the same reference numeral through the several views.

Provided herein is a telemedicine solution, one exemplary embodiment of which improves homecare and customer service while reducing medical costs by allowing patients to remain at home. It should be noted that although the present invention is described with reference to use in the medical field, the present invention has applications to fields where image-assisted analysis is. desired without the need for traveling conventionally required by on-site examination. For example, other conceivable applications would be for mechanical analysis, for peer discussions, or for telecommuting where input is sought from others over a remote distance.

Referring to FIG. 1, the capture-and-storage device 100 of an exemplary embodiment of the present invention utilizes existing telephone lines to provide health care access to remote and rural patients with image-assisted diagnosis. The ability to use low-level communications lines such as POTS ("Plain Old Telephone System") gives the health care diagnostician greater access to patients. Such communications systems are presently used with conventional MODEM devices that allow the computer to transmit information over standard telephone lines. Nevertheless, as communications technologies advance, such as the widespread implementation of ISDN (Integrated Service Digital Network), other telecommunications technologies can be implemented to allow the transfer of multimedia data.

The capture-and-storage device 100 has a portable laptop computer 102, a digital camera 104, and an executable software program 106, which is installed on, and executed by, the laptop computer 102 to provide image capture, transfer, and database storage. An executable program is understood to be a computer program that is ready to run. The term refers to a compiled program that has been translated into machine code in a format that can be loaded into memory and executed by the microprocessor; however, for interpreted languages, the term can simply refer to source code in the proper format.

The laptop computer 102 can include a 5×86 microprocessor operating at about 133 MHZ or other suitable processors, a color display screen 18 sufficient to convey adequate information to the user for analysis, and sufficient random-access-memory (RAM) to accommodate the images.

The digital camera 104 has macro focus and low light capabilities. A suitable digital camera is a model Pixera Professional available from Pixera Corporation of Los Gatos, Calif. It should be noted, however, that as technology advances, faster computers with more powerful microprocessor and graphics capability can be used. The software program 106 loaded into the program memory is executed by the microprocessor of the laptop computer 102 to provide video and audio conferencing capabilities to enable a diagnostician to survey a patient from a remote site. The term "remote" as used herein means not in the immediate vicinity of the computer system 102, the computer system being remotely accessible by another device located in another place (being a room, building, city, state, or country) that is accessible through some type of cable or communications link.

The capture-and-storage device 100 captures high resolution still-images that can also be transmitted to corresponding computer devices connected across the telecommunications path, or transferred using common file transfer techniques associated with computer technology, as is known in the art. These images can be annotated by both parties, and saved or discarded. When saved, the software program 106 saves the images and related patient information in a patient "episode-of-care" folder for patient history and for retrieval purposes.

In another application—such as with rural health care, homecare, long term care facilities, or the like—the capture-and-storage device 100 can be used for data acquisition. For example, a homecare nurse at a patient residence can connect to a physician through a video conferencing session provided by the software program 106. Both parties can have their cameras in use, or just at the patient site. Once in the care session, the nurse or the physician can capture a still image from the remote camera 104. The captured-image can then be shared between the parties and be mutually annotated by each party to discuss care for a particular symptom. Each party has the capability to save an image or images for their records and end the session.

The saved data images are stored in the device 100 database and electronic file cabinet, along with information on the patient, nurse, physician, service date, and capture date of each image. A memo field is also available for both the nurse and the physician to record additional information. The filed information is "hot synchronized" to keep a united record for the health system. Furthermore, additional scanned information pertinent to the patient can be added to the database record at any time, such as prescriptions image, X-ray images, pathology report images, or the like. The term "image" as used herein, refers to a digital representation of a document or other such information.

A description of the software program 106 follows regarding the integrated software solution for capturing multi-media data for organization and transmission with a database.

Figure 2:
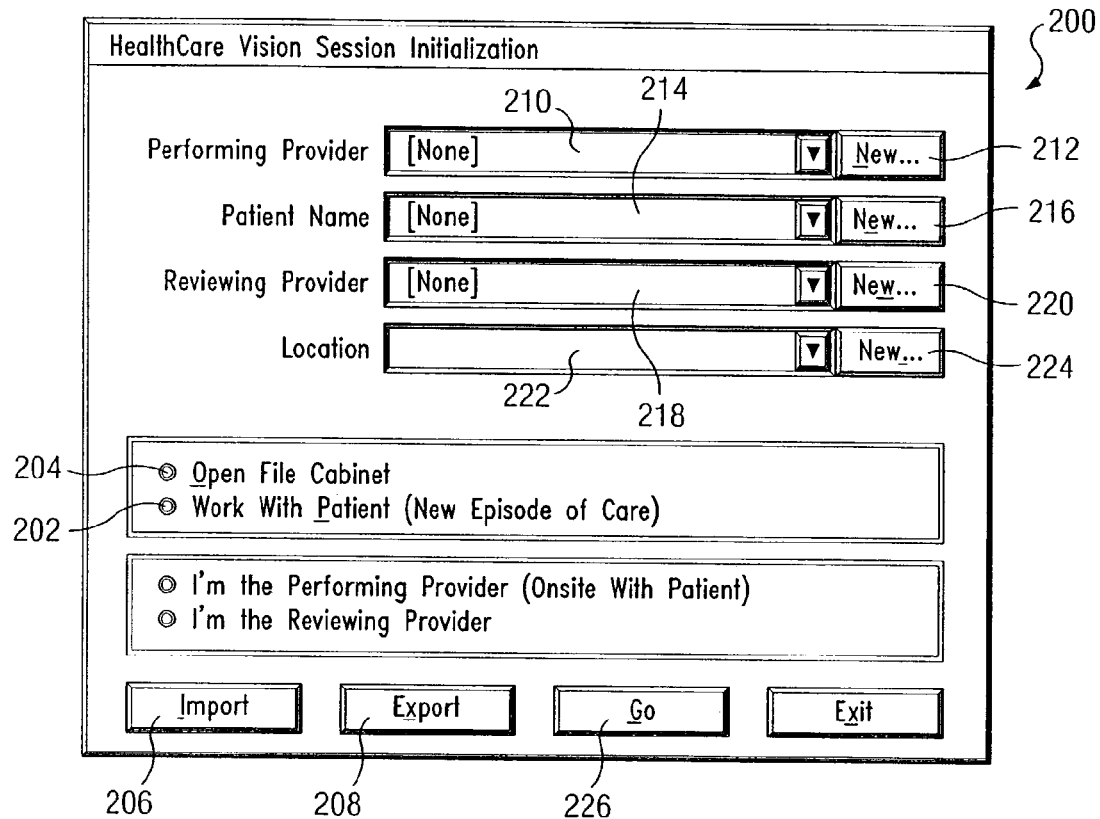
FIG. 2 is an illustration of an exemplary session initialization window.

FIG. 2 shows an exemplary session initialization window 200 upon activation of the device and selection of the software program 106 for execution by the computer 102 (see FIG. 1). The activation of the software program 106 can take place through conventional invocation techniques such as pressing an icon indicating selection of the program or through voice commands via the headset 122. Activating the program 106 loads the database into program memory, and prompts the user to make selections through the session initialization window 200.

Three options are available through the Session Initialization window 200: (I) work with the patient by pressing icon 202; (2) Open_the_File Cabinet function (to look at patient history, make notes, append documents, etc.) by pressing icon 204; or (3) import or export records to or from another device 100 by pressing either icon 206 or icon 208.

With pressing either the icon 202 or icon 204, Work_with_the_Patient function (begin a new episode-of-care), or the Open_the_File_Cabinet functions are selected. If so, then the user selects a Performing Provider (the provider onsite with the patient) for the field 210 from the pick list or adds them by clicking on the "New" button 212, and then selecting a patient name for the field 214 from the pick list or add a Patient by clicking on the "New" button 216. Optionally, a Reviewing Provider (the Provider that will be called) is selected in the field 218 from the pick list or add a Reviewing Provider by clicking on the "New" button 220. Also, as an option a location (the location where the patient is being seen)

is selected in the field 222 from the pick list or adds a location by clicking on the "New" button 224.

With this information in place, and the mode selected through the Open_File_Cabinet icon 204 or through the Work_with_Patient icon 202, the "Open File Cabinet" option invokes the data viewing aspects of the device 100 opening the communications and capture functions, discussed later in detail. The "Work with Patient" function invokes a new episode-of-care, which opens both the data aspects of the device 100 by opening the "electronic file cabinet" and the communications and data capture software packages. The execution of the selected option takes place by pressing the "Go" button 226.

Selecting the import icon 206 or the export icon 208 imports or exports records to or from another device 100. The underlying functions are known to those skilled in the art and are not discussed in detail. The "Import" function is available if imported files are stored on the device 100 and have not been imported. Selecting the import icon 206 initiates importing files from a sending device 100. Files received from the transmitting device are merged with files on the receiving system 100. With the export icon 208 selected, the report files to be exported are copied to a temporary Export directory for file transfer, and are then exported from the device 100 according to a specified date range.

With respect to the "Open File Cabinet" mode and the "Work with Patient" mode, the same information is available for review, analysis, and commentary by the reviewing provider. The difference, however, is that additional data acquisition and communications capabilities are made available through the "Work with Patient" mode.

Figure 3:
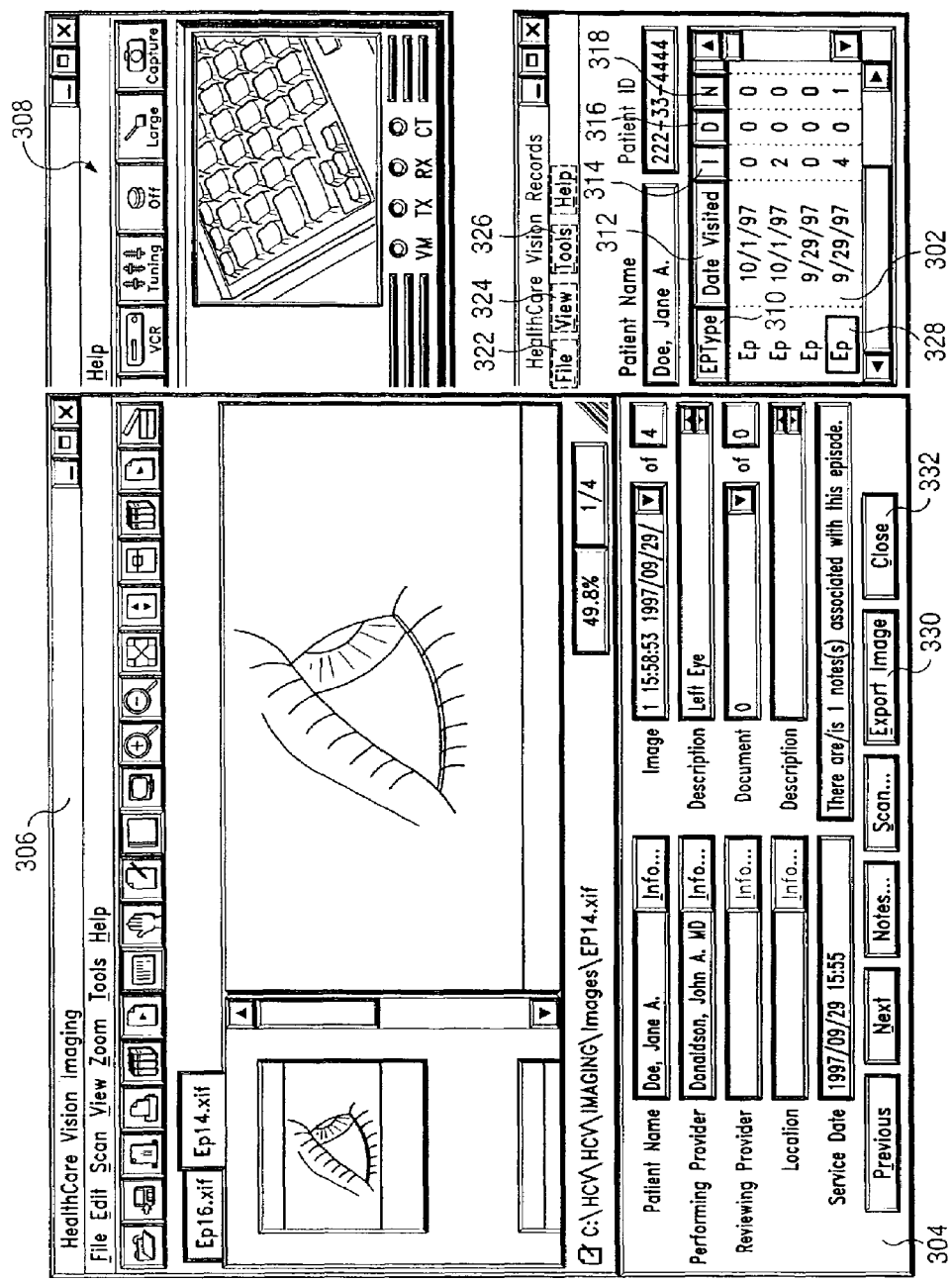
FIG. 3 is an illustration of an exemplary Graphical User Interface ("GUI") for receiving input and for displaying data.

Referring to FIG. 3, shown is a Graphical User Interface ("GUI") 300 displayed on the screen 18. The GUI 300 is provided by the executable program 106 (see FIG. 1). The configuration shown in FIG. 3 is representative of the appearance of the user interface for the device 100 when in the "Open File Cabinet" mode or the "Work with Patient" mode invoked through the Session Initialization window 200 (see FIG. 2).

If the "Open File Cabinet" mode is chosen, the selected patient history (prior episodes) is displayed in a records window 302. An imaging window 306 displays the image(s) associated with the most recent episode-of-care (in this example, one image from a session on 29 Sep. 1997). In this mode, the prior episodes can be accessed and reviewed, or searches conducted on the database.

If the "Work with Patient" mode is chosen, a new episode-of-care for the selected patient is started. The patient and provider names are "written" into the database with the current date (taken from the internal clock of the computer 102). The GUI 300 displays the records window 302, the episode information window 304, an imaging window 306, and a communications-and-image-capture window 308. The records window 302 displays an overview on the data for the current session, and the previous sessions for the patient, if any. The episode information window 304 displays data for the session that entered through the Session Initialization window 200 (see FIG. 2), and the data is updated as the provider session progresses. The image window 306 is initially blank until an image is captured through the controls of the image capture window 308.

A GUI is a type of display format that enables the user to choose commands, start programs, and view lists of files and the operation by pointing to pictorial representations (icons) and lists of menu items on the screen. Choices can generally be activated either with the keyboard 120 or with a mouse. Graphical user interfaces are used on the Apple Macintosh and by such programs as Microsoft Windows, and the OS/2 Presentation Manager.

Additionally, choices may also be activated using a voice-command software package and associated communications headset 122 to provide voice-activation and voice transcription of notes. Such a feature allows the provider to work with the patient to capture, transmit, and store data images without having to resort to manual keystrokes. A further advantage of voice-command is the user-friendly feature available to users having limited computer skills. A suitable voice-command module is available from Verbex Voice Systems, of Edison, N.J.

In FIG. 3, the GUI 300 shows, in a side-by-side orientation, a records window 302, an episode information window 304, an imaging window 306, and a communications-and-image-capture window 308. These windows are invoked through the selection of modes in the session initialization window 200 (see FIG. 2) discussed above in detail.

The term "window," as used in the applications and graphical interface contexts, is understood to be a portion of the screen that can contain its own document or message. In window-based programs such as GUIs, the screen can be divided into several windows, each of which has its own boundaries and can contain a different document (or another view into the same document). It should be noted that the windows of the GUI 200 can be placed in an overlapped orientation.

The GUI 200 provides a data input/output path to a software database, which in conjunction with the keyboard 120 and the headset 122, and mouse if used, a user can provide multimedia information that is readily accessed and updated through the GUI, including graphical image data captured with the digital camera 104.

A software database is an aggregation of data, which is arranged in a number of records or tables, each of which is constructed of fields (or columns) of a particular type, together with a collection of operations that facilitate searching, sorting, recombination, and similar activities. A suitable database is available under the mark ACCESS® from Microsoft, Inc., of Seattle, Wash.

The software database is the organizational aspect of the device 100. Text and graphical data information, or program indexes, are stored in the database for each session or episode-of-care. The database has a series of tables that allow organization and storage on a per-episode basis. In this manner, a vast amount of useful information is conveyed to a user at one time on which to base diagnosis and treatments, as well as the gathering and storage of such information in a concise location. Up to this time, such availability required consulting with numerous physicians and specialists, as well as culling through numerous files and charts to arrive at a suitable treatment. The software database has the following tables:

| No | Table | Description |
|---|---|---|
| 1 | Docs | This table tracks scanned documents and document folders. All data is entered by the software application except for the optional page title, which is entered by the user in the Episode window 204. |
| 2 | Episode | This is the Master Table, which keeps track of image folders, document folders, notes, patients, providers and location information for each visit. All data is entered by the software application. |

| No | Table | Description |
|---|---|---|
| 3 | Images | Keeps track of saved images and their associated information through the JView window 208. All information is entered by the software application except for the optional image title, which is entered by the user in the Episode window 204. |
| 4 | Location | Contains data storage location information. Data is accessed from the Session Initialization, the records window 202, and the episode information window 204. The dialog box fields are the Location_ID, Type, Description, and Facility. |
| 5 | LocType | A sub-table for the Location Table that codifies location information. Values are preloaded by manufacturer and are based on the ANSI ASC X12 data dictionary. |
| 6 | Notes | Contains notes, creator of note and time/date information. Notes are entered by the user in the episode window 204. |
| 7 | Patient | Contains the name, address, and demographic information on patients. Data is entered by the user. This table is accessed from the session initialization window, the records window 202, and the episode window 204. The Patient ID number is the database record key, and is the data field used to tie the database to other health care applications. |
| 8 | PatientIDTypes | A sub-table for the Patient table that contains qualifiers to indicate the type or source of the patient ID number. Values are preloaded by the device manufacturer, and are based on the ANSI ASC X12 data dictionary. |
| 9 | Pharmacy | Sub-table of the Patient table. |
| 10 | Provider | Contains name, address, and demographic informarion on all health care providers. Data is entered by the user. This is accessed from the session initialization screen, the records window 202, and the episode window 204. |
| 11 | ProviderCode | A sub-table for the Provider table that contains qualifiers to indicate the type of provider. Values are preloaded by the device manufacturer, and are based on the ANSI ASC X12 data dictionary. |
| 12 | ProviderIDType | A sub-table for the Provider table that contains qualifiers to indicate the type or source of the provider ID number. Values are preloaded by the device manufacturer, and are based on the ANSI ASC X12 data dictionary. |

Further details concerning the database structure are provided in Appendix A, which is incorporated herein by reference.

The records window 302 provides several fields for accepting and displaying information. In general, the records window 302 is a nexus of the capture-and-storage device 100 in that the functions associated with the episode information window 304, the imaging window 306, and the communications-and-image-capture window 308 are generated by selections and actions taken in this window. In this manner, a centralized record containing text, images, annotations can be created that is complete within itself.

The records window 302 has a Type field 310, which shows whether the session was an Episode (created by using Work-with-Patient mode) or a Document folder. A document folder can be attached to a patient file drawer without being associated with a particular episode. The Date_Visited field 312 shows the date of the session. Sessions are organized in the table from most recent to the oldest. The "I" field 314 shows a numerical count of the number of images in the Episode folder for that session. The "D" field 316 shows a numerical count of the number of scanned document pages in the associated document folder that is part of the Episode for that session. The "N" field 318 shows a numerical count of the number of associated notes for the episode. The Loc field 320 has a two character descriptor of the type of facility where the session was performed. This list. is shown in Appendix A in the LocType table, IDUser column.

When selected, the File Menu 322 of the records window 302 provides several user options. The menus options are Scan, Print, New_Episode_of_Care, or Search_for_Records.

When the Scan option is selected, the user can select "To Patient File" to scan a document or image to a non-Episode folder that is associated globally to the patient (not to a particular Episode). On the other hand, the user can select "To This Episode" to scan a document or image to a Doc folder having the same "x" designator as the Episode and is associated with the current Episode shown in the record window 302. The number of document pages is then displayed in the "D" field 316 of the Episode shown in the record window 302.

When the Print option is selected, the user can print a total record or a data only record. If the user chooses to print Data-and-Images, then each image and each document associated with the selected Episode is printed. The database information sheet that is printed contains: (a) Episode ID; (b) Episode Type; (c) Date/Time Visited; (d) Patient ID; (e) Patient Name; (f) Performing Provider Name; (g) Reviewing Provider Name; and (h) Notes, each with Provider Name and the Date/Time of entry.

Each image in the Episode folder is printed on a separate page with a header that displays "Captured Image x of x from Episode x." Each page in the associated document folder is printed on a separate page with a header the displays "Document x of x from Episode x."

If the user selects the New_Episode_of_Care option, then the user is returned to the session initialization window 200 to select new options or to exit the system.

If the user selects the Search_for_Records option, the user is able to key in search terms that are searched for in the database. If a narrower search is desired, search categories can be used, such as providers and patients, a specific episode of care between a specific beginning and end date, or based on a location identifier or location description.

Still referring to FIG. 3, the View Menu 324 is selected to allow a user to view additional information for a selected episode shown in the record window 302. If the "Episode Information" option is selected, the episode information window 304 is spawned. The episode information window 304 is discussed later in detail.

Also, the "Patient Information," "Provider Information," "Location Information" or "Notes" options can be selected from the View Menu 324. Upon selection, a display window is invoked to show the detailed information associated with these tables.

The Tools Menu 326 of the records window 302 allows a user to add new patients, providers or locations to the database. These additions can also be done in the session initialization window 200.

As discussed above, when the "Episode Information" option is selected from the View Menu 324, the episode information window 304. By highlighting a different Episode line with the window cursor 328 in the listing of the records window 302, the information displayed in the episode information window 304 and the imaging window 306 will change accordingly to reflect data stored with respect to that episode.

The episode information window 304 displays database information, and accepts database information. This window is titled "Current Episode" under the Work with Patient mode and is automatically displayed when the application begins. This window is titled "Episode Information" under the Open File Cabinet mode and is opened by choosing the View Episode Information option in the records window 304.

This window functions mainly on buttons and pull-down menus. It has the following data fields:

a. Patient Name—This shows the name of the selected patient. Pressing the "Info" button next to this field pops-up the Patient screen. The Patient information can also be accessed from the records window 302.
b. Performing Provider—This shows the name of the Performing Provider for the Episode. Pressing the "Info" button next to this field pops-up the Provider screen. The Provider information can also be accessed from the records window 302.
c. Reviewing Provider—This shows the name of the Reviewing Provider (if one is active) for the Episode. Pressing the "Info" button next to this field pops-up the Provider screen. The Provider information can also be accessed from the records window 302.
d. Location—This shows the description of the Location (if one is active) for the Episode. Pressing the "Info . . . " button next to this field pops-up the Location screen. The Location information can also be accessed from the records window 304.
e. Service Date—Displays the date and type of the Episode. This is taken from the system clock of the computer 102.
f. Image of x—Displays the number of images for the Episode, with the
g. individual number and date/time stamp in the first box and the total number of images for the Episode in the second box. Using the down arrow-displays information on the other images in the folder. Selecting an image by moving the arrow, changes the information in this window and refocuses the image viewed in the imaging module window.
h. Description—The "Description" box directly beneath the "Image" box displays the title of the currently displayed image. Clicking the mouse in the box allows input of data. This box displays the optional title of the currently selected image.
i. Document of x—Displays the number of pages in the optional Document folder for the Episode, with the individual number and date/time stamp in the first box and the total number of documents for the Episode in the second box. Using the down arrow displays information on the other documents in the folder. Selecting a document by moving the arrow changes the information in this window and refocuses the document viewed in the imaging window 306.
j. Description—The "Description" box directly beneath the "Document" box displays the title of the currently displayed document page. Clicking the mouse in the box allows input of data. This box displays the optional title of the currently selected document page.
k. Notes—The last field on the window shows how many notes are associated with the Episode. Notes are accessed through the "Notes" button or the records window 302.

The image communications functions of the GUI 300 is carried out through the "Export Image" key 330, which selects the current image in the imaging window 306 and sends it to the communications-and-image-capture window 308 for transfer to a connected party. If in the event the communications-and-image-capture window 308 is not active, the window will open and the image will be displayed within.

The "Close" key 332 closes the episode information window 304. If the device 100 is in the "Work with Patient" mode, then the program returns to the session initialization window 200 (see FIG. 2). Otherwise, if the program is in the "Open File Cabinet" mode, the "Close" key 332 simply closes the episode information window 304.

Figure 4A:
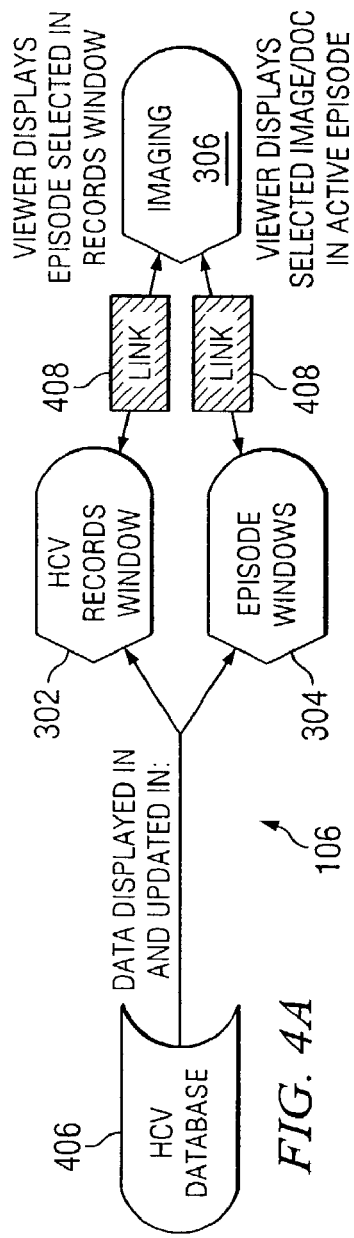
FIGS. 4A-4C are exemplary program structure diagrams regarding the interconnection of the program modules through connecting links.
Figure 4B:
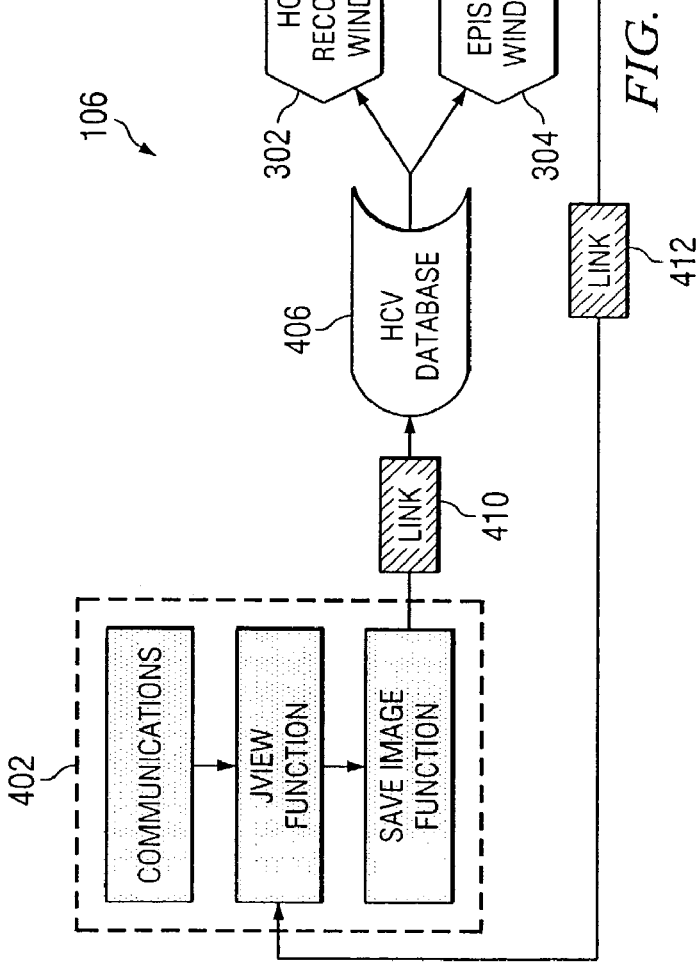
Figure 4C:
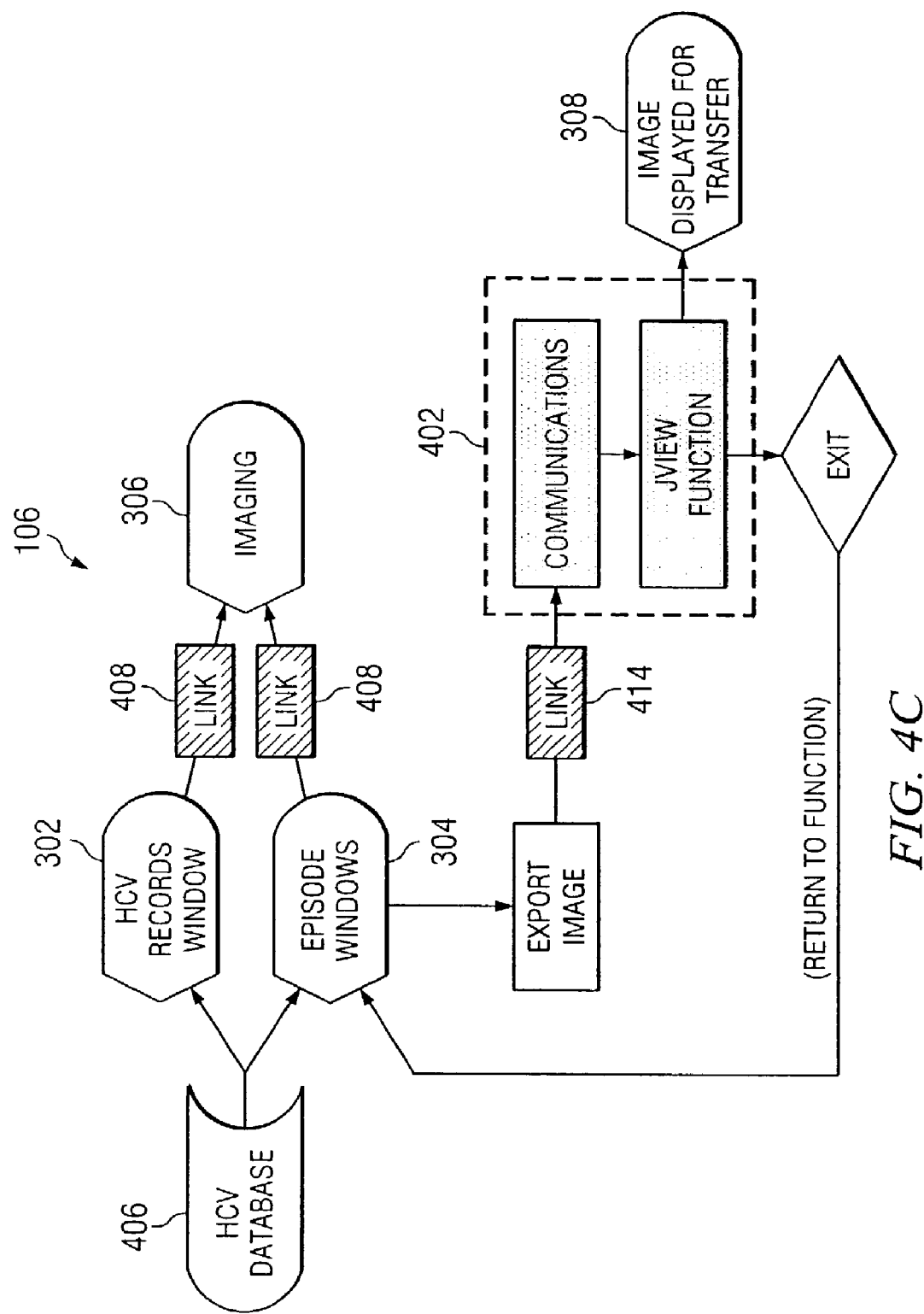

FIGS. 4A through 4C are program structure diagrams regarding the interconnection of the program modules through connecting links. The software program 106 initially referred to with respect to FIG. 1 is an integrated solution that has several program function modules to provide multimedia information formats to a user. The software program 106 has a communications module 402, an imaging module 404, and a database 406, which is discussed in detail above and with respect to Appendix A. Connecting links 408, 410, 412, 414, and 416 respectively interconnect the communications module 402 and imaging module 404, respectively, for integration with. the database 406. Such links between the program modules are known to those skilled in the art.

The communications module 402 captures images, can establish a phone connection to a similar device 10, can share images with a similar device 10, and can save images for later recall. A suitable communications module is available under the product name AudioVision from Smith Micro Software of Aliso Viejo, Calif.

The AudioVision product provides two-way video and audio communications over the Internet, intranet, or standard POTS lines using standard analog modem connections. The operation of such products is known to those skilled in the art and accordingly, is not discussed in further detail. The communications module is activated when the "Work with Patient" option is selected, invoking the communications-and-image-capture window 308 (see FIG. 3).

The communications module 402 has a JView plug-in function, which is a high resolution image capture, annotate, and store program. The JView function program can capture a 640×480×24 bit true-color image through the digital camera 104 (see FIG. 1), and is linked with connecting link 390, illustrated in Appendix C, Diagram 3, that enables the JView module to pass data to the imaging module 340.

When JView is selected, the high resolution viewer is activated and overlays most of the screen as illustrated in Appendix A, Screen Diagram 15. The communication module 320 can operate with and without an established telecommunications connection between the two parties. If there is a telecommunications connection, then additional features are made available.

Referring to FIG. 4A, the imaging module 404 is an electronic filing cabinet with document and image filing and scanning capabilities. A imaging module is available under the product name View Wise from WhetStone Technologies of Park City, Utah. The imaging module serves as links 408 between the records window 302 and the episode window 304. The imaging module 404 displays the image/document folder selected in the record window 302, and the selected image or document of the episode information window 304.

Referring to FIG. 4B, when an image is saved through the JView function of the communications-and-image-capture window 308, the link 410 is activated to pass the image and associated information (size, compression ratio, date/time stamp) to the database 406 for storage. The captured image is placed in the episode folder of for the patient and is given a unique identifier for retrieval and identification purposes. If multiple images are saved for an episode, they are all written to the episode folder. The software application 106 automatically gives each data image a unique filename. When JView is exited, the user is prompted whether to save any images that have not already been saved.

The record window 302 is updated to reflect the image was captured in the "I" field 314 (see FIG. 3). The episode information window 304 is similarly updated to display the active image. The program 106 then returns to the communication module 402 to conduct further image processing when called by the user.

During the saving of an image to a patient Episode of Care folder, the images are transferred from the communications module 402 to the imaging module 404 (the electronic file cabinet).

As the saved images are imported into the file cabinet, they are converted into a XIF format, with each image being a JPEG file. The typical JPEG compression is set at 75, but the user has the option to alter this. If altered on the communication module 402 side, the connecting link 410 will pass the new value to the image module, and the data image will be saved accordingly. The time/date stamp becomes a permanent part of the image and cannot be removed. The file formats were chosen to maintain the quality of the image and to reduce storage requirements. A 640×480×24 bit image is 921,600 bytes while a typical compressed JPEG for storage is from about 30,000 to about 50,000 bytes.

Referring to FIG. 4C, shown is the program structure for opening previously saved data images for analysis or retransmission. Again through the JView plug-in function of the communications module 402, link 414 allows the export of a stored image from the database 406 to the communications module 402. When the retrieved image is in the possession of the communications module 402, the image can be transmitted to a connected reviewer. This is done with the connecting link 395 on the Current Episode window that "exports" the currently displayed image from the imaging window 306, invokes the JView function, and displays the image in the communications-and-image-capture window 308. The user then selects "Transmit" to send the image to a reviewer. The image is opened with the same attributes it had when it was saved. The time/date stamp is displayed and the quality is set to the value it had when originally saved.

The user can opt to review a previous episode before taking new images. For example, this might be important if they want to capture a wound from the same angle as it was taken during the last patient visit. To select a previous episode, they can either highlight the episode in "Date Visited" field 312 in the records window 302 to a previous episode, or older sessions can be viewed accordingly. Once a previous episode is selected, the imaging window 306 displays the images in that folder, and the episode information window 304 displays information about that episode (see FIG. 3).

Figure 5:
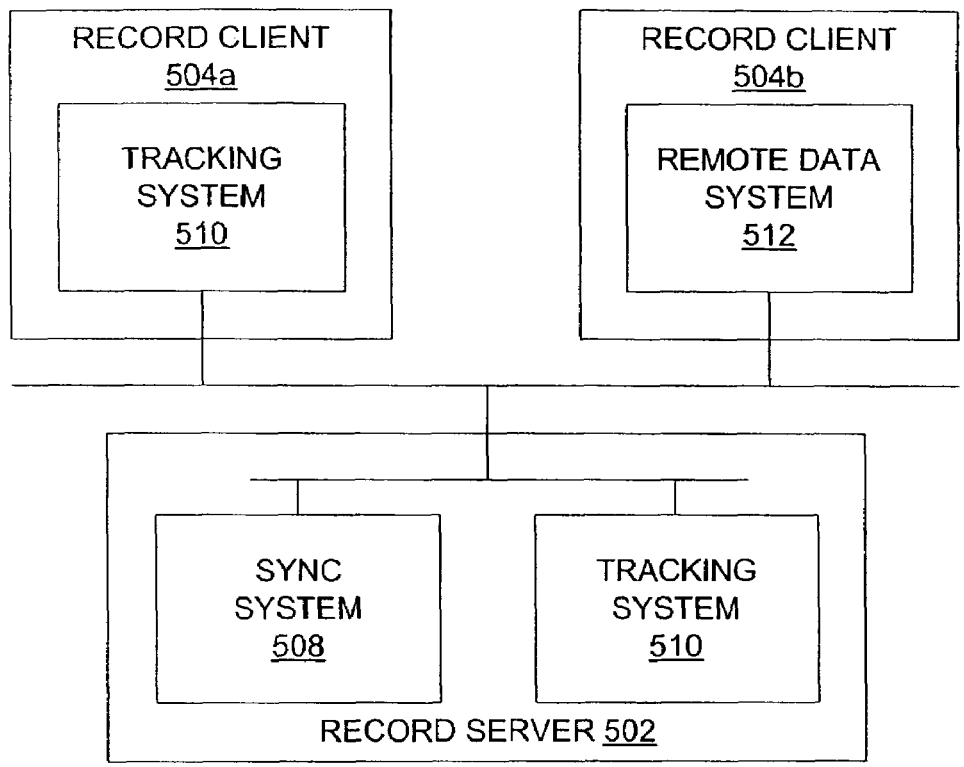
FIG. 5 is a diagram of a system for providing telemedicine services in accordance with an exemplary embodiment of the present invention.

FIG. 5 is a diagram of a system 500 for providing telemedicine services in accordance with an exemplary embodiment of the present invention. System 500 allows physicians to ensure the continuity and integrity of medical records so as to enable them to use telemedicine to treat patients without incurring significant risk of legal liability or other serious problems.

System 500 includes record server 502 which can be implemented in hardware, software, or a suitable combination of hardware and software, and which can be one or more software systems operating on a general purpose server platform. As used herein, a software system can include one or more objects, agents, threads, line of code, subroutines, separate software applications, two or more lines of code or other suitable software structures operating in two or more separate software applications, on two or more different processors, or other suitable software architectures. In one exemplary embodiment, a software system can include one or more lines of code or other suitable software structures operating in a general purpose software application, such as an operating system, and one or more lines of code or other suitable software structures operating in a specific purpose software application. In another exemplary embodiment, a software system can include one or more lines of hypertext markup language (*.HTML) or other suitable software operating in a general purpose web browser system, so as to create a specific purpose system receiving information input from a user.

Record server 502 is coupled to record clients 504a through 504b by communications medium 514. As used herein, the term "couple", and its cognate terms such as "couples" and "coupled", can include a physical connection (such as through a copper conductor), a virtual connection (such as one or more randomly assigned memory locations of a data memory device), a logical connection (such as through one or more logical devices of a semiconducting circuit), a wireless connection, other suitable connections, or a suitable combination of such connections. In one exemplary embodiment, systems and components are coupled to other systems and components through intervening systems and components, such as through an operating system of a general purpose processing platform. Communications medium 514 can be a local area network, a wide area network, the public switched telephone network, the Internet, a frame relay, a wireless network, an optical network, other suitable communications media, or a suitable combination of such communications media.

Record server 502 transfers medical record data files to record clients 504a through 504b. To ensure that medical records sent to record clients 504a through 504b will not be inadvertently misfiled or confused by practitioners with those other patients, record server 502 includes sync system 508. Sync system 508 transmits a synchronization data file to record client 504a or 504b prior to transmission of medical record data files. In one exemplary embodiment, sync system 508 can transmit the entire medical record data file for a patient to record client 504a or 504b, such that record client 504a or 504b stores the latest version of the entire medical record data file regardless of whether any version of that file exists on record client 504a or 504b. In another exemplary embodiment, sync system 508 can first determine which medical record data file or files a record client 504a or 504b has for a patient, and can then transmit only files or portions of files that have been changed, new files, or other suitable files. In this manner, sync system 508 ensures that the medical record data files stored on record client 504a and 504b are the most recent medical files, and further that sufficient files exist to particularly identify any patient, so as to prevent inadvertent misdiagnosis, misplacement or misfiling of medical record data files, or other problems.

Record server 502 also includes tracking system 510. Tracking system 510 is used to track access to medical record data files. In one exemplary embodiment, tracking system 510 includes an algorithm that creates a unique tracking access code number based upon the previous value of the tracking identification number, the date of access, the location of access, and other suitable data, such that the modification history for the medical data file can be determined from the tracking access code number. Tracking system 510 further prevents predetermined portions of the medical record data file from being modified. In another exemplary embodiment, medical diagnostic data, physician comment data, and other suitable data can be encapsulated such that any attempt to alter or modify the data will be prevented or detected.

Tracking system 510 on record server 502 can coordinate with tracking system 150 on record client 504a so that files that have been transmitted to record client 504a are checked when record client 504a returns the files to record server 502. In this matter, any modifications or attempt to modify sealed medical record data will be detected. Likewise, record server 502 and record client 504*a* can be configured to prevent access to medical records except through record server 502 and record client 504*a*, such as by using encryption and decoding systems.

Record client 504*b* includes remote data system 512. Remote data system 512 can be implemented in hardware, software, or suitable combination of hardware and software, and can be one or more software systems operating on a general purpose processing platform. Remote data system 512 generates audio data, audiovisual data, graphical data, text data, or other suitable data and transmits it to record server 502, so that the data can be viewed by an operator at that location. Likewise, record server 502 can forward the data to record client 504*a* or other suitable systems for remote viewing by others. Remote data system 512 interacts with tracking system 510 and sync system 508, such that the remote data can be encapsulated as it is generated, at predetermined times, stored with diagnostic data received from a doctor, or otherwise combined. In one exemplary embodiment, tracking system 510 can receive the graphical image data or other data from remote data system 512, can provide that data to record client 504*a*, and can also receive diagnostic data from practitioners at record client 504*a*. The graphical image data can be encapsulated separately from the diagnostic data received from each doctor, and all three sets of data can then be encapsulated to prevent subsequent modification. In this manner, a clear record of the medical treatment, diagnostic data, and other information can be kept. The graphical image data described herein, such as in regards to the description of the systems and methods shown in the FIGS., can be JPEG format data, Digital Imaging and Communications in Medicine (DICOM), Tagged Image File Format (TIFF) graphic image formats, or other suitable image data formats. Likewise, the image data can be generated using View Wise, Image Viewer, Microsoft compatible media and imaging annotation/editing tools, or other suitable image data processing tools. In one exemplary embodiment, a viewer can select image data, video sequence data, x-ray-data, ultrasound data, or other suitable data for examination, annotation, comparison, or other suitable purposes.

Record clients 504*a* and 504*b* can be implemented in hardware, software, or a suitable combination of hardware and software, and can be one or more software systems operating on a general purpose processing platform. In one exemplary embodiment, record clients 504*a* and 504*b* can operate on a server physically located at a medical facility or remote treatment facility, can be application services providers (ASP) providing services to terminals at different medical facilities, or can be implemented in other suitable manners.

In operation, system 500 facilitates the provision of telemedicine services by ensuring medical record data file integrity and continuity. Medical record data file integrity is ensured by sealing diagnostic data, doctor comments, and other suitable data to prevent subsequent modification of the data. Medical record data file continuity is ensured by keeping a track of all access to the medical record data file so that it can be readily determined whether a medical record was accessed, when it was accessed, who accessed it, and what was done to the medical record data file. In this manner, system 500 allows a medical record data file to be generated and maintained as a permanent part of a patient's medical record, thus minimizing any legal liability for loss of medical record data, intentional or inadvertent modification or manipulation of medical record data, or other similar problems typically encountered in the prior art.

Figure 6:
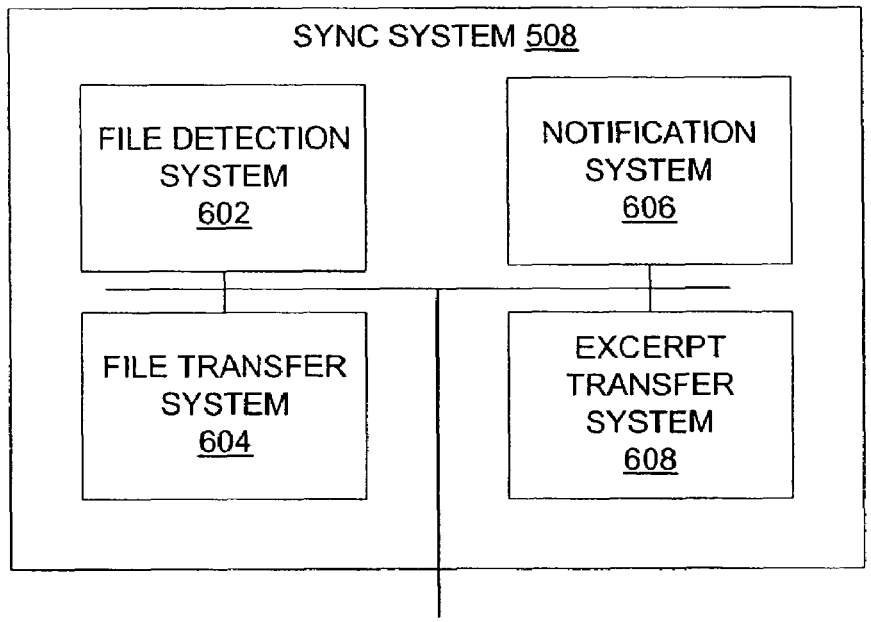
FIG. 6 is a diagram of a system for providing file synchronization functionality in accordance with an exemplary embodiment of the present invention.

FIG. 6 is a diagram of a system 600 for providing file synchronization functionality in accordance with an exemplary embodiment of the present invention. System 600 includes sync system 108 and file detection system 602, file transfer system 604, notification system 606, and excerpt transfer system 608, each of which can be implemented in hardware, software, or a suitable combination of hardware and software, and which can be one or more software systems operating on a general purpose processing or server platform.

File detection system 602 interfaces with a record client 504 or other suitable systems to determine whether a medical record data file for a patient is present on such system. In one exemplary embodiment, file detection system 602 can determine which of a plurality of medical record data files exists, the version of such medical record data files, and other suitable information such as size and access date so as to determine whether modifications have been made to the files, whether such modifications are authorized, or other suitable information. File detection system 602 can then transfer the latest version of files, new files, or other suitable files to a record client 504 or other suitable systems. File detection system 602 can also interface with a file storage system operating on system 600 to update file access and status records.

File transfer system 604 can transfer medical record data files from sync system 508 to record client 504 or other suitable systems, and can likewise transfer the files or receive the files from such systems and store them on sync system 508 or system 600. File transfer system 604 keeps track of where medical record data files have been transmitted, the time of transmission, and the contents of the medical record data files at the time of transmission, such that it can be readily determined which practitioners were given access to the medical record data file and what was in the file when they were given access. File transfer system 604 can also be used to determine what additional information may have been added to a medical record data file after it was transmitted to a practitioner and before it was returned to system 600.

Notification system 606 generates notification data such that practitioners at a record client 504 or other suitable systems can be made aware of the presence of a file or a file excerpt. In one exemplary embodiment, notification system 606 operates in conjunction with excerpt transfer system 608 so as to notify a practitioner that an excerpt is available for review and comment. In this exemplary embodiment, notification system 606 can send a pager message, email message, phone message, or other suitable message to a doctor or other medical professional requesting that doctor to view a file, such as by accessing a website, an FTP server, or by receiving an email with a medical record excerpt attachment, or by other suitable methods, and can also receive confirmation from such medical professional when the medical record excerpt has been reviewed and returned. Notification system 606 can also notify a local physician of the availability of a medical record data file and when such file was flagged for review by the medical professional, and can status a file unreviewed if the medical professional declines or otherwise indicates that review of the record will not be performed.

Excerpt transfer system 608 allows a portion of a medical record, such as encapsulated graphic image data, x-ray image data, audio data, audiovisual data, graphic data, text data, ultrasound data, or other suitable data, to be accessed by a predetermined practitioner and for that practitioner to enter comments or other suitable data. In one exemplary embodiment, excerpt transfer system 608 is used to receive diagnosis input from remotely-located practitioners, such as review of x-ray data by a surgical expert, internal organ expert, or other suitable experts. Excerpt transfer system 608 can be used to prevent transfer of the entire medical record when only a portion of the medical record needs to be transferred. Excerpt transfer system can operate in conjunction with notification system 606, file transfer system 604, and file detection system 602 to ensure that minimal data transfer requirements are performed in order to facilitate the receipt of diagnostic data from remote practitioners.

In operation, system 600 allows medical record data files to be synchronized prior to transmission, facilitates the complete transfer of medical records, and tracks the status of such medical records so as to determine whether modifications to records have been performed without proper authorization. System 200 thus helps to prevent inadvertent misplacement of medical records, and also helps to prevent the need for transmitting entire medical record data files when only excerpts of the medical record data files need to be transmitted. System 200 can also be used to detect when medical record data files have been improperly modified.

Figure 7:
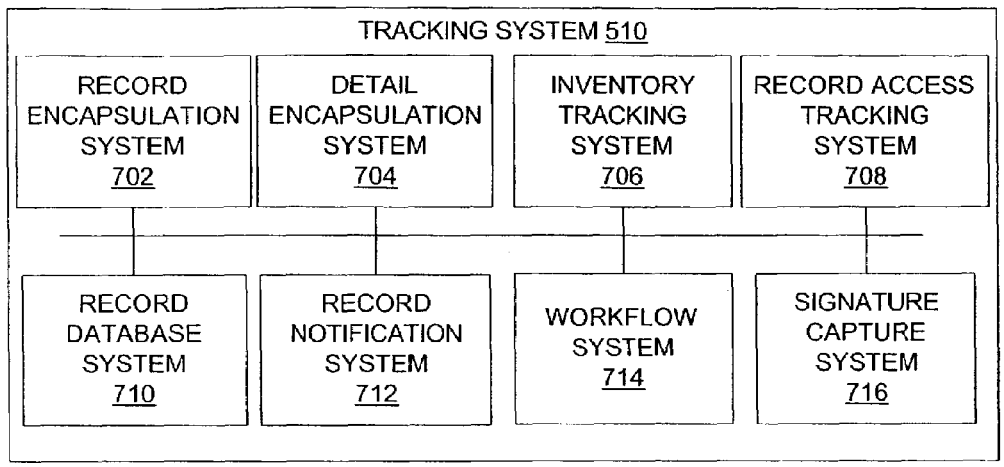
FIG. 7 is a diagram of a system for providing medical record data file tracking functionality in accordance with an exemplary embodiment of the present invention.

FIG. 7 is a diagram of a system 700 for providing medical record data file tracking functionality in accordance with an exemplary embodiment of the present invention. System 700 includes tracking system 510 and record encapsulation system 702, detail encapsulation system 704, inventory tracking system 706, record access tracking system 708, record database system 710, record notification system 712, workflow system 714, and signature capture system 716, each of which can be implemented in hardware, software, or a suitable combination of hardware and software, and which can be one or more software systems operating on a general purpose server platform.

Record encapsulation system 702 can encapsulate an entire medical record data file for a patient so as to maintain the integrity of the entire medical record data file. In one exemplary embodiment, record encapsulation system 702 includes encryption algorithms that generate a value based upon the exact data structure of the entire medical record data file, such that any modifications to the medical record data file can be detected. Record encapsulation system 702 can also buffer the medical record when it is accessed, such that if an attempt is made to modify the medical record data file prior to closing it, then a suitable flag can be generated and the previous version of the medical record can be stored separately from the modified version. Record encapsulation system 702 can thus be used to notify an operator of record tampering without alerting the party that has tampered with the record of the notification.

In one exemplary embodiment, sync system 508, excerpt transfer system 608, tracking system 510, record encapsulation system 702, and other suitable systems can be used as a point-to-point live consultation system, such as to allow a physician to consult with a patient at a remote site, two physicians to consult where one of the physicians is with the patient, two physicians to consult using medical record data, or other suitable point-to-point consultation functionality.

Detail encapsulation system 704 receives diagnostic data, comment data, or other suitable medical record data file data and performs separate encapsulation of such data. In one exemplary embodiment, detail encapsulation system 704 can encapsulate graphic image data, x-ray data, sonogram data, or other suitable data so that inadvertent modification of such data is not performed. Likewise, detail encapsulation system 704 can buffer detail data and detect whether any changes have been made, such as through a suitable encryption algorithm. In this manner, detail encapsulation system 704 can be used to store the original and modified detail data so as to determine whether tampering with data has occurred.

Inventory tracking system 706 can be used to keep track of inventory at a remote location. In one exemplary embodiment, inventory tracking system 706 can be implemented in conjunction with remote data system 512, such as to track the number of pharmaceutical batches that have been stored and are ready for dispensing. Other suitable inventory tracking functionality can be provided.

Record access tracking system 708 performs record access tracking for parties accessing medical record data files through record encapsulation system 702 or detail data through detail encapsulation system 704. In one exemplary embodiment, record access tracking system 708 performs predetermined operations on the data field of the files, on preselected portions of such data fields, or on other suitable software data structures, and can generate record tracking data that indicates the status of part or all of the medical record data file prior to processing it with record access tracking system 708. This record tracking data can be compared to previous record tracking data values such as by sync system 508 or other suitable systems to determine whether modification to part or all of a medical data record file has occurred. In this manner, record access tracking system 708 helps to maintain the integrity and continuity of medical record data.

Record database system 710 stores local record data for medical record data files. In one exemplary embodiment, record database system 710 can coordinate with sync system 508 and tracking system 510 or other suitable systems operating on a record client 504 to determine whether to store a new file as a new version of the medical record data file, replace an existing medical record data file, flag data records as having been improperly modified, or perform other suitable database functions.

The record data stored by record database system 710 can be organized as one or more files or tables, where each file or table has one or more data fields. The data fields can include common data fields, and the files or tables can be associated with each other so as to form a database. The following exemplary files or table structures can be used, and all the data fields provided can be used, a subset of the data fields can be used, some or all of the data fields can be supplemented with other suitable data fields, or sets of other suitable data fields can be used. Likewise, other file or table structures can be used that combine the data fields provided herein in other suitable manners.

One exemplary file or table structure includes vital sign data fields such as a vital sign reading identification number; an episode identification number; systolic blood pressure data; diastolic blood pressure data; pulse rate data; pulse oximetry data; temperature data; bronchial capacity data; bronchial peak flow volume data; spirometry test data; spirometry test type data; blood glucose reading average; blood glucose reading count; height in feet; height in inches; weight in pounds; electro-cardio gram data; and time/date modified data.

Another exemplary file or table structure includes audioclip data fields such as an audioclip identification number; an episode identification number; audioclip name and location; audioclip type designation; audioclip time/date created data; and an audioclip instance number.

Another exemplary file or table structure includes demographics data fields such as patient identification alpha/numeric; provider identification alpha/numeric; demographic survey scribe; patient age data; patient gender data; patient religion data; patient ethnicity data; patient level of education data; patient insurance coverage data; patient household income data; number of household occupants; patient familiarity with telemedicine data; time/date modified; and the number of years the patient has smoked.

Another exemplary file or table structure includes document identification data such as a document identification number; episode identification number; document description data; document creation date; and a document instance number.

Another exemplary file or table structure includes episode data such as an episode identification number; episode type; patient identification alpha/numeric; performing provider alpha/numeric; reviewing provider alpha/numeric; episode creation date; episode image Tag Image File Format (TIF) name and path; episode document TIF name and path; episode creation location; episode diagnosis created; episode cpt code assignment; episode prescription created; new data flag for file transfer; raw audit information; audit code generated from raw audit info; audit index for file transfer; and an episode billing status.

Another exemplary file or table structure includes fetal worksheet data such as a worksheet identification number; episode identification number; worksheet instance number; examination type; patient identification alpha/numeric; patient name (last, first, m.i.); examination date; performing provider identification alpha/numeric; performing provider name (last, first, m.i.); patient's intake indication; patient's age; last menstrual period; gestational age; times pregnant; times given birth; patient abort history; single/multiple fetus; multiple designation type; fetal heart activity; fetal extremeties activity; fetal respiration activity; fetal presentation grade; normal amniotic fluid data; hydro amniotic fluid data; oligo amniotic fluid data; variable amniotic fluid data; anterior placenta position; posterior placenta position; fundal placenta position; placenta condition; placenta grade; cranium identification data; spine identification data; post fossa identification data; ventricles identification data; heart 4 chambers identification data; left VOT identification data; right VOT identification data; fluid GI identification data; bladder identification data; right kidney identification data; left kidney identification data; male gender identification data; female gender identification data; 3 vessel cord identification data; umbilicus identification; extremeties identification; face identification; amniotic fluid volume grade; tone grade; reactivity grade; movement grade; respiration grade; sum of bio elements; sum of bio grades; bi-parietal diameter; bi-parietal age; bi-parietal percentile; bi-parietal associated image number; head circumference measurement; head circumference age; head circumference percentile; head circumference associated image number; abdominal circumference measure; abdominal circumference age; abdominal circumference percentile; abdominal circumference associated image number; long femur bone measurement; long femur bone age; long femur bone percentile; long femur bone associated image number; crown/rump length measurement; crown/rump length age; crown/rump length percentile; crown/rump length associated image number; fetal sac measurement; fetal sac age; fetal sac percentile; fetal sac image number; average age; total cardial diameter; total cardial age; total cardial percentile; total cardial image number; humerus length measurement; humerus length age; humerus length percentile; humerus length associated image number; effective fetal weight; estimated date of delivery; fetus systolic blood pressure; and fetus diastolic blood pressure data.

Another exemplary file or table structure includes glucometer reading data such as a reading identification number; episode identification number; patient identification alpha/numeric; blood glucose measurement; and a measurement time and date.

Another exemplary file or table structure includes image data such as an image identification number; episode identification number; image description; image creation time/date; image instance number; image quality setting; subjective notes; objective notes; assessment notes; and plan notes.

Another exemplary file or table structure includes location data such as a location identification number; location description; userid; and facility data.

Another exemplary file or table structure includes location type data such as a location type identification number; location type description; and a userid.

Another exemplary file or table structure includes note data such as a note identification number; episode identification number; provider identification alpha/numeric; note creation time/date; and note text.

Another exemplary file or table structure includes patient data such as a patient identification alpha/numeric; patient identification type; prefix; firstname; middlename; lastname; suffix; date of birth; address; city; state; postal code; home phone; work phone; patient pharmacy identifier; patient insurance information; patient diagnosis history; patient prescription history; patient profile modification history; disease state management note history; weight; height feet; height inches; systolic blood pressure minimum; systolic blood pressure maximum; diastolic blood pressure minimum; diastolic blood pressure maximum; heart rate minimum; heart rate maximum; pulse oximetry minimum; pulse oximetry maximum; temperature minimum; temperature maximum; blood glucose minimum; blood glucose maximum; bronchial capacity minimum; bronchial capacity maximum; peak flow minimum; and peak flow maximum.

Another exemplary file or table structure includes patient identification type data such as a patient type identification number; patient type name; and a patient type mask.

Another exemplary file or table structure includes pharmacy data such as a pharmacy identification number; pharmacy name; phone number; and a fax number.

Another exemplary file or table structure includes provider data including a provider identification alpha/numeric; provider identification type; provider activity code; firstname; middlename; lastname; suffix; organization name; address; city; state; postal code; work number; modem number; fax number; password; prefix; hcv privileges; ip address/machine name; provider profile modification history; and a global patient access flag.

Another exemplary file or table structure includes provider code data such as a provider activity code and code description.

Another exemplary file or table structure includes provider identification type data such as an identification number; identification name; and identification mask.

Another exemplary file or table structure includes site data such as a federal identifier; company name; address; city; state; zip code; primary user identifier; voice number; and fax number.

Another exemplary file or table structure includes spirometry data such as a spirometry identification number; episode identification number; patient identification alpha/numeric; test time/date; test type; test sequence number; test date; mouth piece number; physician name; forced vital capacity (FVC); forced expiratory volume (FEV) 0.5 second; forced expiratory volume 1st second; forced expiratory volume 3rd second; percentage ratio of FEV (timed) to FVC; peak expiratory flow rate; forced expiratory flow @ 25%; forced expiratory flow @ 50%; forced expiratory flow @ 75%; forced expiratory flow @ middle of test; forced inspiratory vital capacity; forced inspiratory vital capacity @ 0.5 second; forced inspiratory vital capacity @ 1 second; forced inspiratory vital capacity (FIV) @ 3 second; peak inspiratory flow (FIF) rate; FIF @ 50%; FIF @ 75%; FIF between 200 ml and 1200 ml. 1000 ml measure; percentage ratio of expiratory time to volume; maximum voluntary ventilation; maximum total ventilation; respiratory rate; slow vital capacity; body temperature and pressure, saturated; and room temperature during test.

Another exemplary file or table structure includes video-clip data such as identification data; episode identifier; a drive or server path where the clip is located; the type of clip; time stamp data; and page number data.

Another exemplary file or table structure includes activity log data such as an identifier; the action that is being logged; user; filename; time of activity; and send/receive status data.

Another exemplary file or table structure includes data for interfacing with the Epi Info™ system available from the U.S. Department of Health and Human Services Center for Disease Control. The data fields in the Epi Info™ can be changed by third parties over time, and allow the tracking of data for epidemiologic and statistical purposes, including but not limited to the tracking of head circumference data, body-mass index data, and other suitable data. In one exemplary embodiment, Epi Info™ or other suitable systems can be used to calculate and graphically depict historical trends and values of biometrics (as well as to compare biometrics to other individuals, groups, the national averages, or other suitable data). Biometrics can include but are not limited to blood pressure, temperature, heart rate, pulse oximetry, spirometry, weight, height, glucometry, fetal profile data and measurements, gestational age, heart and cardio rhythm data, and other suitable measurement data. Such calculations can use input patient data and readings and can be compared to national and professional standards, averages, clinical standards, or other suitable data sets. In addition, historical patient-specific or episode-related data can be input for graphical representations, such as for documenting disease outbreaks for a specific patient as a function of time. Cross computational calculations and other calculations depicting ratios can also or alternatively be employed.

Record notification system 712 generates notification data to notify a party that a record has been received and that the record should be reviewed. In one exemplary embodiment, a medical record data file or an excerpt is transmitted with the name of a practitioner, an email address, a pager number,'or other suitable data. Record notification system 712 logs the received files or excerpts and notifies the practitioner in one or more predetermined manners, such that diagnostic treatment can be performed without requiring the participation of all involved parties. In this manner, record notification system 712 facilitates the processing of telemedicine diagnostic data, such as by allowing doctors to diagnose such data when they have available time, and does not require practitioners to be present when the diagnostic data is being acquired. Record notification system 712 can thus be used in a local mode to also facilitate the coordination of medical advice after diagnostic data has been acquired.

Workflow system 714 manages workflow data, such as workflow data for prepping a tote at a pharmacy that contains one or more prescriptions, workflow data. for filling prescriptions, workflow data for verifying that a prescription has been properly filled, or other suitable workflow data. In one exemplary embodiment, workflow data can track the number of errors that a given employee makes, can track the time that an employee requires to complete workflow steps, or can otherwise provide management data for determining an employee's optimal skills, for tracking employees with substandard skills, and for otherwise managing pharmacy workflow. Likewise, workflow system 714 allows the status of unfilled pre-scriptions to be readily determined, allows the amount of time for a prescription to be filled to be determined, and provides other suitable functions.

Signature capture system 716 allows signature data to be obtained and stored in a database in lieu of paper logs, and further allows patients who have refused to sign, have not signed, or who need to sign again to be readily determined and tracked. In one exemplary embodiment, signature capture system 716 can be implemented in conjunction with a palm pilot or other suitable palm top or portable processor, such as to allow patients at a pharmacy drive-through window or other suitable locations to execute a privacy policy acceptance, refill reminder acceptance, third party data release acceptance, or to otherwise allow sensitive personal information to be used for reasons other than treatment, payment, or health care operations. Likewise, a signature verifying the receipt of the prescription by the patient or a third party, the receipt of counseling, or other suitable data can also be obtained. Signature capture system 716 can also generate reports showing patients that have refused to sign, patients with signatures that have expired, patients that signed an approval for an older version of a privacy policy, patients that have authorized the release of their information to third parties, patients having pending or past-due refills and who have provided authorization to be reminded, or other suitable reports.

In operation, system 700 allows medical record data files to be tracked and access to such medical record data files or medical record data contained within such medical record data files to be tracked, coordinated and controlled so as to prevent unauthorized modification of data, to maintain the integrity of the data file, and to ensure continuity of the medical record data file. System 700 thus allows telemedicine services and other suitable services requiring access to a medical record data file to be provided without incurring the risks posed by prior art systems.

Figure 8:
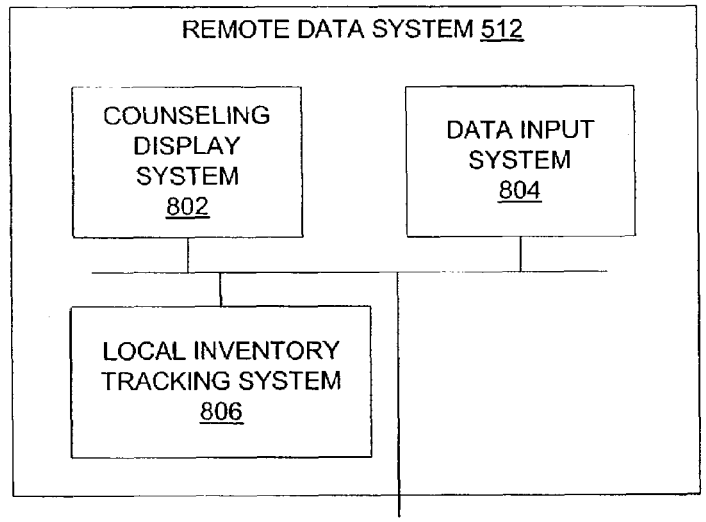
FIG. 8 is a diagram of a system for providing remote data input in accordance with the exemplary embodiment of the present invention.

FIG. 8 is a diagram of a system 800 for providing remote data input in accordance with the exemplary embodiment of the present invention. System 800 includes remote data system 512 and counseling display system 802, data input system 804, and local inventory tracking system 806, each of which can be implemented in hardware, software, or a suitable combination of hardware and software, and which can be one or more software systems operating on a general purpose processing platform.

Counseling display system 802 can generate graphic image data, text data, comment data, or other suitable data and can transmit that data to a record server 502 or other suitable systems for processing. Counseling display system 802 thus allows remote access to audio data, audiovisual data, graphic data, text data, x-ray data, sonogram data, or other suitable data. In one exemplary embodiment, counseling display system 802 can be used to allow a pharmacist or other medical professional to provide counseling to patients located at a record client 504b, such that the pharmacist, physician or other suitable medical practitioner does not have to be physically present in order to provide counseling of the patient. Counseling display system 802 can also interface with detail encapsulation system 704, record encapsulation system 702, or other suitable systems of record server 502 to allow the data to be stored and encapsulated to prevent modification or loss of the data. In this manner, both the data provided to the doctor to facilitate diagnosis and counseling and the data received from the doctor in response to the provided data can be stored either on remote data system 512, at a record server 502, at both locations, or in other suitable locations.

Data input system 804 allows data to be input to assist with counseling provided through counseling display system 802 or for other suitable purposes. In one exemplary embodiment, data input system 804 includes a still image camera, sonogram data generating equipment, x-ray scanning equipment, or other suitable data input systems that can provide data from a remote location to a physician at a record server 502, at another record client 504, or other suitable systems. In another exemplary embodiment, data input system 804 can receive data such as a bar code or other identifying data on a package of pharmaceutical supplies, and this information or data can be used to identify both the type of drug stored within the package, and also the identity of the patient for whom the pharmaceutical materials are being provided. It may then be determined by data input system 804, remote data system 512, record server 502, or other suitable systems whether the patient has received the pharmaceutical materials before or otherwise requires counseling. Data input system 804 can then coordinate with counseling display system 402 to allow a practitioner to provide counseling to the patient or otherwise ensure that all necessary procedures for providing the pharmaceutical supplies to the patient have been followed.

Local inventory tracking system 806 can keep track of the number of packages of pharmaceuticals or other suitable packages or materials that have been dispensed by a record client 504, remote data system 512 or other suitable systems. Local inventory tracking system 806 can coordinate with an inventory tracking system 706 of a record server 502, another record client 504, or other suitable systems so as to ensure that the amount of pharmaceutical materials provided to a remote location is controlled. In one exemplary embodiment, remote data system 512 is implemented on a record client 504b located in a remote pharmaceutical dispensing facility that does not have a licensed pharmacist on site. Remote data system 512, record client 504 and record server 502 can then be used to counsel a patient at the remote facility if the patient has not received the drugs before, and to store such counseling so as to generate a record showing that the patient received sufficient counseling as may be required by law or good medical practice. In this manner, system 800 facilitates telepharmacy services, by generating record data that can be used to respond to regulatory authorities if they ever question whether regulatory policies have been followed, such as a requirement for the counseling of a patient when they receive a prescription drug for the first time.

In operation, system 800 allows data to be gathered from remote locations where there is no licensed practitioner, and then allows the licensed practitioner to access that data and to provide comments, diagnostic information or other suitable information. System 800 can thus be used to assist with telepharmacy services, with remote telemedicine counseling, or other suitable processes.

Figure 9:
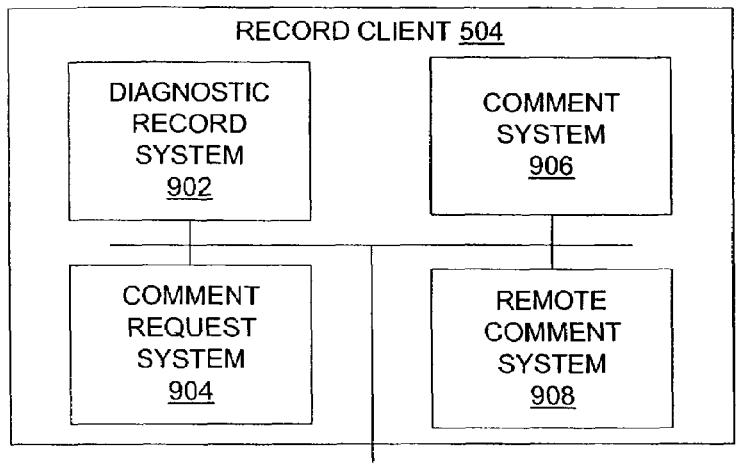
FIG. 9 is a diagram of a system for providing record client functionality in accordance with an exemplary embodiment of the present invention.

FIG. 9 is a diagram of a system 900 for providing record client functionality in accordance with an exemplary embodiment of the present invention. System 900 includes record client 504 and diagnostic record system 902, comment request system 904, comment system 906, and remote comment system 908, each of which can be implemented in hardware, software, or a suitable combination of hardware and software, and which can be one or more software systems operating on a general purpose server platform.

Diagnostic record system 902 generates diagnostic record data for inclusion in a medical record data file. In one exemplary embodiment, diagnostic record system 902 can include (but is not limited to) a handheld still image generating camera, a handheld video image generating camera, eye/ear/nose and throat imaging equipment, arterialscopic or other invasive imaging equipment, x-ray imaging equipment, ultrasound equipment, an intracavity transducer, an abdominal transducer, a vital signs monitor, a glucometer, an electrocardiograph, a larynagoscope, a spirometer, an opthalmoscope, a dermascope, sonographic imaging equipment, audio monitoring equipment such as for listening to heartbeats or other sounds, or other suitable diagnostic equipment. Diagnostic record system 902 generates the diagnostic record data, and can encapsulate some or all of the data, such as segments of the data that are relied on by a surgeon or practitioner to render advice, or other suitable data.

Comment request system 904 can be used to request comments on some or all of a medical record data file. In one exemplary embodiment, comment request system 904 can interact with a remote comment system 908 operating on another record client 504, systems operating on a record server 502 or other suitable systems to request comment data from one or more remotely located practitioners. Comment request system 904 can then track whether such comments have been received, and can coordinate with comment system 906 to store the comments and encapsulate them for inclusion in the medical record data file.

Comment system 906 receives comments, such as from a local practitioner or from a remote practitioner, and associates those comments with diagnostic record data or other suitable data. Comment system 906 can also encapsulate the comments at the completion of the diagnostic session for inclusion in the medical record data file.

Remote comment system 908 coordinates with other systems to receive comments or requests for comments. In one exemplary embodiment, a remote comment system 908 can receive a request for comment and can notify a local physician of the request for comment, such as by email, pager message, file transfer protocol (FTP), or other suitable procedures. In this manner, remote comment system 908 can operate in an "unattended" mode, such that FTP protocol or other suitable protocols for the transfer of large files can be initiated without requiring an operator to be present at the receiving end to initiate the transfer. Remote comment system 908 can then receive the comments from the local physician, can generate displays of graphical diagnostic record data or other suitable data, can support real time video conferencing, or can perform other suitable functionality. Remote comment system 908 can also coordinate with remote comment system 906 to store such diagnostic data locally, such as by storing record affiliation data, so that the local physician or practitioner can keep a record of the advice rendered and the data on which that advice was based.

In operation, system 900 allows practitioners to generate diagnostic records, view existing diagnostic records, view existing comments, and store new comments. System 900 further allows practitioners to coordinate with other practitioners to receive comment data on records, select portions of the record for access by or transmission to such remote practitioners, or perform other suitable functions. In this manner, system 900 facilitates the provision of telemedicine services by ensuring record integrity and continuity.

Figure 10:
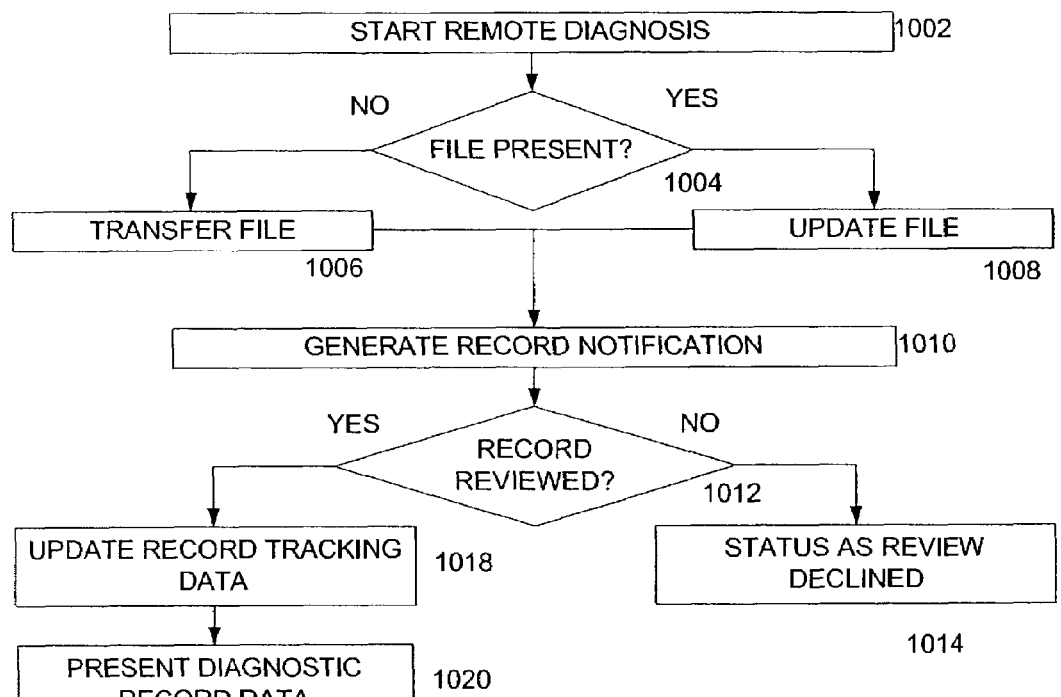
FIG. 10 is a flow chart of a method for providing file synchronization and tracking in accordance with an exemplary embodiment of the present invention.

FIG. 10 is a flow chart of a method 1000 for providing file synchronization and tracking in accordance with an exemplary embodiment of the present invention. Method 1000 begins at 1002 where a remote diagnosis is initiated. In one exemplary embodiment, the remote diagnosis can be initiated when the physician logs on, requests initiation of the remote diagnosis, receives the request for initiation of the remote diagnosis, or otherwise indicates that they will participate in a remote diagnosis. For example, remote diagnosis may start when a physician determines that another physician should receive the medical record data file and provide diagnostic data/comments. The method then proceeds to 1004 where it is determined whether the medical record data file is present at the remote site. If it is determined that the medical record data file is not present, the method proceeds to 1006 where the file is transferred. The method then proceeds to 1010. Otherwise, if it determined that the medical record data file is present, the method proceeds to 1008 where any portions of the medical record data file that are not present can be transferred, updated with the most recent data, or other suitable procedures can be used. Likewise, 1008 can be bypassed when portions of the medical record data file are not used. The method then proceeds to 1010.

At 1010, record notification data is generated. For example, a list identifying all of the medical record data files that have been received can be generated that alerts the practitioner to the receipt of the records in the order in which they were received, in order of priority, in order or urgency, or in other suitable orders. Likewise, an email, pager message, or other suitable record notification message can also or alternatively be generated. The method then proceeds to 1012.

At 1012, it is determined whether the record has been reviewed. For example, the record notification procedure can be implemented a predetermined number of times, after which time the medical record data file will receive a status of not having been reviewed or of having review declined. If it is determined that the record has not been reviewed at 1012, then the method proceeds to 1014 where the medical record data file status is assigned. In one exemplary embodiment, review may be declined when a physician has received a medical record improperly, is not familiar with the patient, is no longer treating the patient, or in other suitable circumstances. If it is determined at 1012 that the record has been reviewed, the method proceeds to 1016.

At 1016, record tracking data is updated. For example, when the medical record data file is opened, an algorithm can be used to modify tracking data that identifies the most recent access to the record, the time and date, the location, the name of the physician accessing the record, the size of the file, the structure of the file, or other suitable data. The method then proceeds to 1018 where the diagnostic record data is presented to the practitioner for review and comment.

In operation, method 1000 provides for synchronization and tracking of medical record data files to ensure the integrity and continuity of the file. Method 1000 can be used to prevent the inadvertent misclassification or misidentification of medical record data files. Method 1000 further provides for tracking of all access to medical record data files, to maintain an audit trail capability so that all practitioners who had access to the record and their comments made at that time can be determined. Likewise, it can also be determined whether a physician was requested to access a record and declined to do so.

Figure 11:
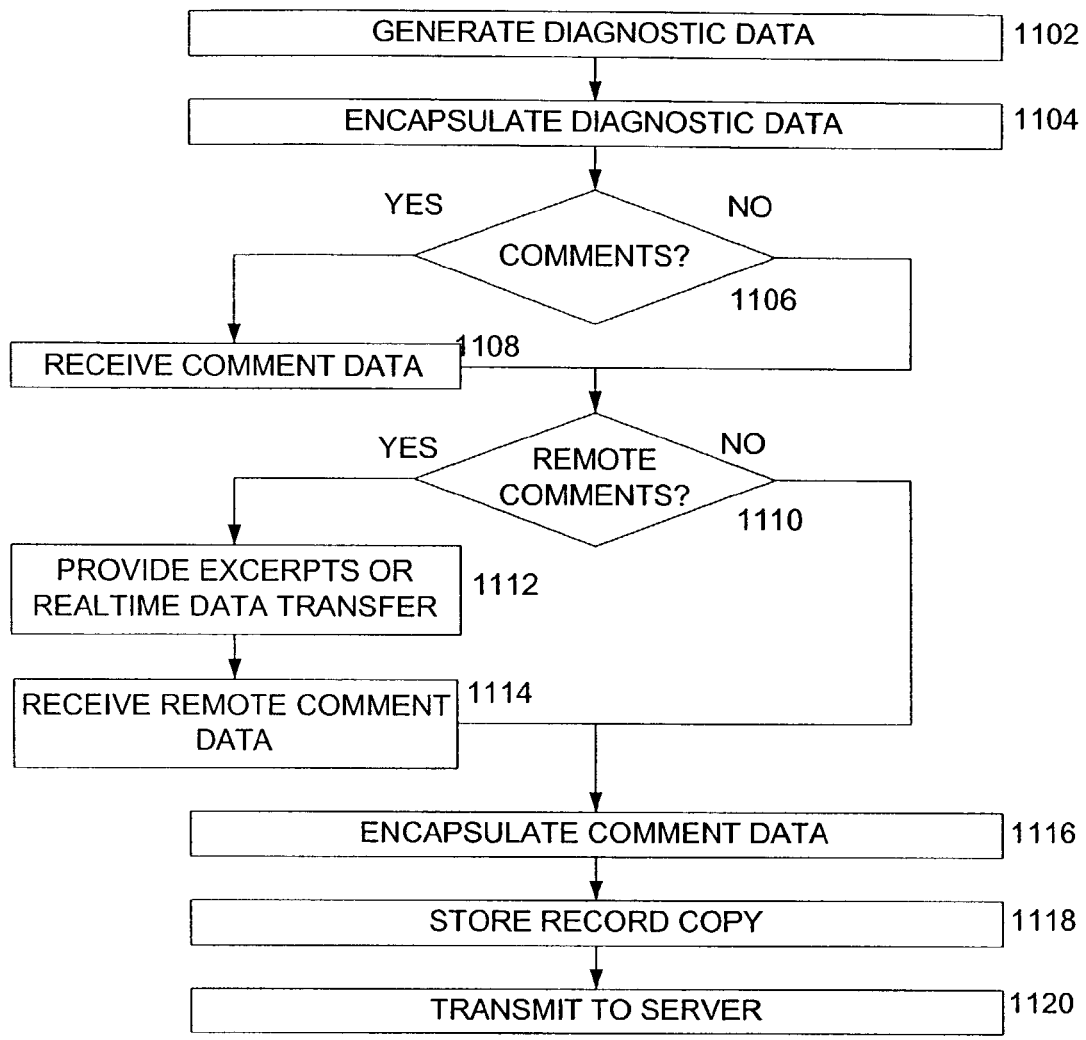
FIG. 11 is a flow chart of a method for generating and encapsulating diagnostic data in accordance with an exemplary embodiment of the present invention.

FIG. 11 is a flow chart of a method 1100 for generating and encapsulating diagnostic data in accordance with an exemplary embodiment of the present invention. Method 1100 begins at 1102 where diagnostic data is generated. In one exemplary embodiment, the diagnostic data can be generated by creating photographic image data, x-ray data, ultrasound data, specialized graphic image data, or other suitable data. The method then proceeds to 1104.

At 1104, the diagnostic data is encapsulated. In one exemplary embodiment, the diagnostic data can be encapsulated by including it in a format that is proprietary such that any attempt to access the data with a nonproprietary image viewer or other data viewer will result in the corruption of the data or damage to the data. Likewise, the data can be encapsulated in a manner that causes the data to be buffered and where any modifications are stored along with the prior unmodified image or data, so that notification data can be generated and the attempt to tamper with the record can be detected. The method then proceeds to 1106.

At 1106, it is determined whether comment data is being provided with the encapsulated diagnostic data. If it is determined at 1106 that comment data is not being received, the method proceeds to 1110. Otherwise, the method proceeds to 1108 where the comment data is received. The method then proceeds to 1110.

At 1110, it is determined whether remote comment data is requested or is being provided. If it is determined that no remote comment data is being requested or provided, the method proceeds to 1116. Otherwise, the method proceeds to 1112 where excerpts or real time data transfer is provided. In one exemplary embodiment, the diagnostic data that has been encapsulated is provided to the remote location in real time, such as by providing a live video feed as the data is being encapsulated. Likewise, the data can be stored as a file and transmitted for later viewing by a remotely located practitioner. Likewise, the comment data received at 1108 can be transmitted, and can be encapsulated prior to transmission. The method then proceeds to 1116.

At 1116, the remote comment data is received. The remote comment data can be received in real time with the comment data received at 1108, can be received in a time-shifted manner, such that the remote comment data is encapsulated, or other suitable procedures can be used. The method then proceeds to 1116.

At 1116, the comment data is encapsulated. If the comment data has previously been encapsulated, such as at 1108, then the combined set of comment data from the various sources can be encapsulated at 1116 to form a comment data record. The method then proceeds to 1118 where a record copy of the medical record data file is stored. For example, each time the medical record data file is transmitted between a server and a record client, the medical record data file can be stored such that a sequence of modifications to the medical record data file can be determined and verified. Likewise, the latest version of the medical record data file can be stored at the record client, and the record server can be used to store all historical versions of the file or other suitable procedures can be used. The method then proceeds to 1120.

At 1120, the medical record data file is transmitted to a medical record server for storage and maintenance. Likewise, the server can perform any continuity or integrity checks, such as to determine whether attempts have been made to tamper with the medical record data file, whether parties have had access to the file after the file was provided to the practitioner, or other suitable procedures can be performed.

In operation, method 1100 allows diagnostic data to be generated and encapsulated and further allows comment data from one or more practitioners to be associated with the diagnostic data. All diagnostic data and comment data can then be encapsulated to provide a consistent and traceable medical record.

Figure 12:
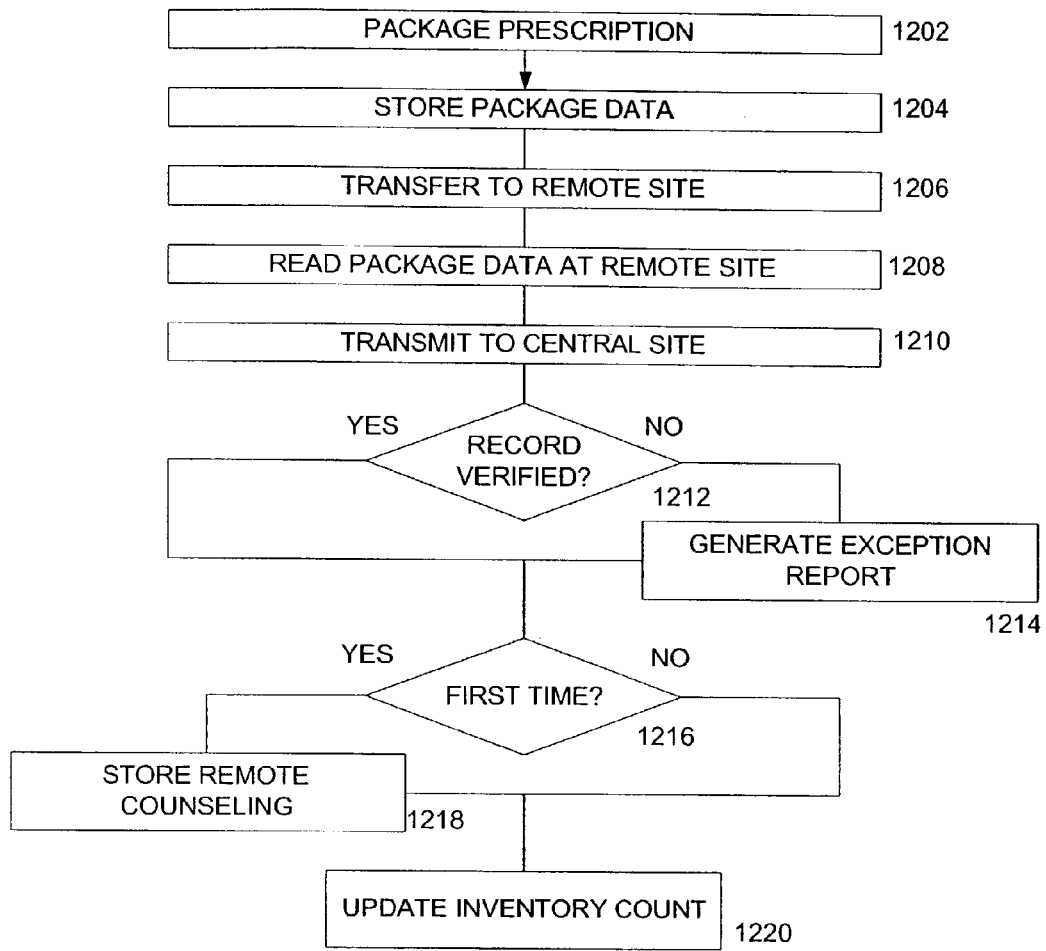
FIG. 12 is a flow chart of a method for providing telepharmacy services in accordance with an exemplary embodiment of the present invention.

FIG. 12 is a flow chart of a method 1200 for providing telepharmacy services in accordance with an exemplary embodiment of the present invention. Method 1200 begins at 1202 where a prescription is packaged. In one exemplary embodiment, the prescription can include sealed packaging having a predetermined number of doses of medicine. The prescription can further be packaged in response to a noticed that is generated based upon the number of remaining prepackaged prescriptions at a remote location, or in response to other suitable data. The method then proceeds to 1204.

At 1204, the package data is stored. Package data can include a package identifier, the number of doses of medicine in the package, the strength, the brand, the location which will receive the package, patient data, and other suitable data. The method then proceeds to 1206.

At 1206, the package is transferred to a remote site. The remote site can be a facility that does not have a licensed practitioner onsite but which has personnel that have been trained to operate telepharmacy equipment or other suitable equipment. The method then proceeds to 1208.

At 1208, the package data is read at the remote site. In one exemplary embodiment, a patient can request to have a prescription filled, and the package can be removed from a secured storage area at that time and read by a package data reader. Patient data can also be received at that time, such as identification data, prescription data, insurance data, or other suitable data. The method then proceeds to 1210 where the data read from the package is transmitted to a central site. The method then proceeds to 1212.

At 1212, it is determined whether the record has been verified. For example, the client prescription data and the package data must match, the package data must indicate that the proper package has been received, that the package is at the proper site, and other suitable verification. If the record is verified, the method proceeds to 1216. Otherwise, the method proceeds to 1214 where an exception report is generated. For example, the exception report may include direct notification to the remote site that an error has been committed and a request for correction, record verification data can be generated that indicates that an improper activity may be occurring at the remote site with a flag for follow up that does not notify personnel at the remote site, the proper authorities can be notified, or other suitable procedures can be implemented. The method then proceeds to 1216.

At 1216, it is determined whether the patient has received this prescription before. If the patient is receiving the prescription for the first time, the method proceeds to 1218 where remote counseling data is stored. The remote counseling data can include audiovisual data generated at a central site and at a remote site, where the patient is given advice on how and when to take the medicine and any questions that the patient has may be answered. The remote counseling data is stored in a manner that allows the data to be readily audited by legal authorities in order to verify that any legal requirements for dispensing pharmaceuticals are being followed. The method then proceeds to 1220 where inventory count data is updated. The inventory count data can be used to track the number of remaining packages of pharmaceuticals at the remote location, the expiration dates of the packages, the rate of use of the packages, and other suitable data so that additional packages can be prepared and shipped as needed.

Figure 13:
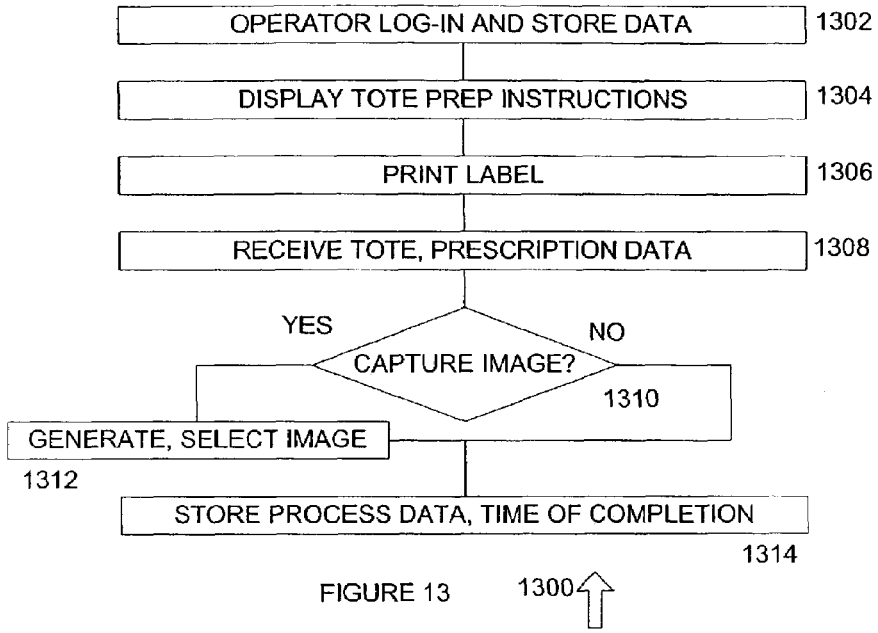
FIG. 13 is a flow chart of a method for workflow processing in accordance with an exemplary embodiment of the present invention.

FIG. 13 is a flow chart of a method 1300 for workflow processing in accordance with an exemplary embodiment of the present invention. Method 1300 allows pharmacy workflow to be managed so as to ensure that quality is being maintained while allowing efficiency to be increased.

Method 1300 begins at 1302, where an operator logs in and data storage is performed. In one exemplary embodiment, operator log-in can include scanning an ID badge, entering a user identifier and a corresponding password, or other suitable processes that can be used to track the operator who is performing the workflow functions. The data stored at 1302 can include a tote identifier that is used to identify a group of prescriptions, operator identification data, start time data, and other suitable data. The method then proceeds to 1304.

At 1304, tote preparation instructions are displayed for preparing the tote or other receptacle that is used to hold the prescriptions. In one exemplary embodiment, the instructions can include scanning the tote identifier (if not already done), entering data into an electronic file from a written prescription, printing a label of the entered prescription data, capturing an image, and performing other processes that are used to prepare the tote and the prescriptions therein for subsequent filling by pharmacy personnel. The method then proceeds to 1306.

At 1306, a label for the prescription is printed. In one exemplary embodiment, the label can include a label for the prescription bottle, a label for an accompanying set of advisory materials, or other suitable labels. The method then proceeds to 1308 where the tote and prescription data are received, such as to enter the data requested at each step of the instructions. The method then proceeds to 1310.

At 1310, it is determined whether it is necessary to capture an image, such as an image of the handwritten prescription, an image of a pharmaceutical (such as for verification purposes where an image has not previously been provided), or other suitable images. If it is determined that an image is not required, the method proceeds to 1314 where the process data, identification data for each of the prescriptions in the tote, the time of completion, and other suitable data is stored. If an image is required, the method proceeds to 1312, where one or more images are generated and selected for storage. In one exemplary embodiment, the image can be generated using a digital camera, such as by placing a handwritten prescription in a predetermined location and then by generating one or more sets of image data until a legible image of the handwritten prescription is generated. In this manner, scanning of the prescription is not required. The method then proceeds to 1314.

In operation, method 1300 allows totes or other receptacles to be prepared that are used to hold one or more prescriptions while the prescriptions are being filled by pharmacy personnel. Method 1300 allows a series of instructions to be displayed and the responses to each set of instructions to be stored, so as to allow errors to be detected, the time for processing each prescription to be monitored, and other useful functions to be performed.

Figure 14:
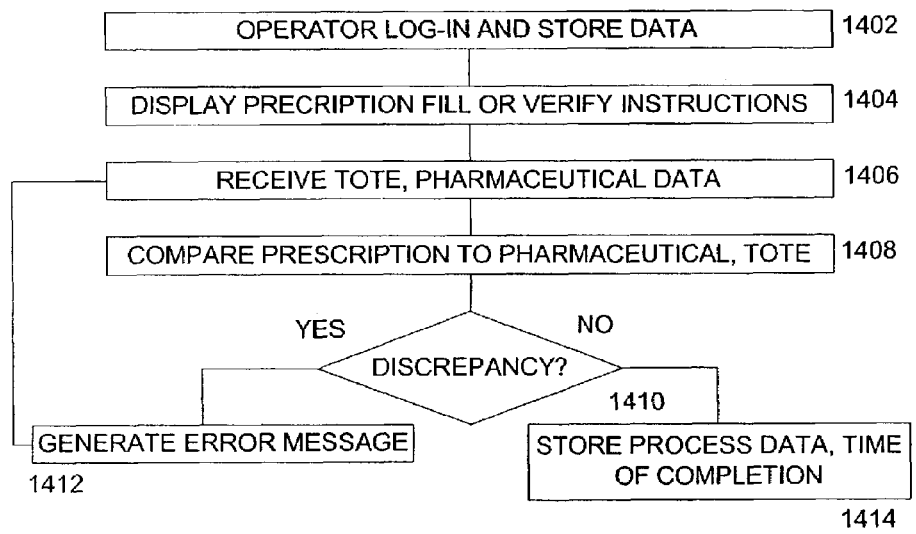
FIG. 14 is a flow chart of a method for prescription fill or verification processing in accordance with an exemplary embodiment of the present invention.

FIG. 14 is a flow chart of a method 1400 for prescription fill or verification processing in accordance with an exemplary embodiment of the present invention. Method 1400 allows pharmacy workflow to be managed so as to ensure that quality is being maintained while allowing efficiency to be increased.

Method 1400 begins at 1402, where an operator logs in and data storage is performed. In one exemplary embodiment, operator log-in can include scanning an ID badge, entering a user identifier and a corresponding password, or other suitable processes that can be used to track the operator who is performing the workflow functions. The data stored at 1402 can include a tote identifier that is used to identify a group of prescriptions, operator identification data, start time data, and other suitable data. The method then proceeds to 1404.

At 1404, instructions for filling prescriptions or performing verification are displayed, depending on the process being performed. In one exemplary embodiment, the instructions can include scanning the tote identifier (if not already done), scanning a prescription label, interfacing with one or more robotic systems that retrieve bottles of pharmaceuticals from predetermined locations and transport them to personnel who are filling the prescriptions, scanning a label on a bottle of pharmaceuticals, and performing other processes that are used to prepare the prescriptions or perform verification of prescriptions that have already been prepared. The method then proceeds to 1406.

At 1406, the tote and prescription data are received, such as by entering the data requested at each step of the instructions. The method then proceeds to 1408, where the prescription data is compared to the pharmaceutical data. In one exemplary embodiment, the prescription data from the label can be compared to the data from the bottle of pharmaceuticals, the prescriptions from the tote prep stage can be compared to the prescriptions scanned at 1406, the prescription data entered at the tote prep stage can be compared to the handwritten prescription data, or other suitable comparisons can be made. If it is determined that a discrepancy exists between the prescription and pharmaceutical data at 1410, the method proceeds to 1412 where an error message is generated, such as a notification that the pharmaceutical data does not match the prescription data. Otherwise, the method proceeds to 1414 where the process data, time of completion, and other suitable data is stored.

In operation, method 1400 allows one or more prescriptions to be filled by pharmacy personnel, and allows the filled prescriptions to be verified for correctness. Method 1400 allows a series of instructions to be displayed and the responses to each set of instructions to be stored, so as to allow errors to be detected, the time for processing each prescription to be monitored, and other useful functions to be performed.

Figure 15:
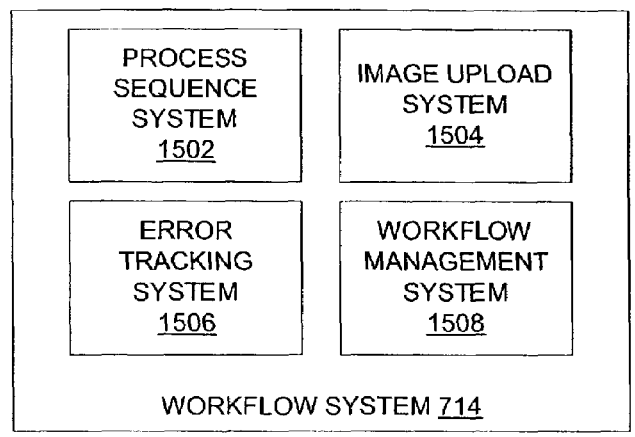
FIG. 15 is a diagram of a system for workflow management in accordance with an exemplary embodiment of the present invention.

FIG. 15 is a diagram of a system 1500 for workflow management in accordance with an exemplary embodiment of the present invention. System 1500 allows pharmacy workflows to be tracked and managed to increase the reliability and efficiency of pharmacy operations.

System 1500 includes workflow system 714 and process sequence system 1502, image upload system 1504, error tracking system 1506 and workflow management system 1508, each of which can be implemented in hardware, software, or a suitable combination of hardware and software, and which can be one or more software systems operating on a general purpose processing platform. Process sequence system 1502 provides process sequence data to an operator and generates indication data when each process sequence step has been completed. In one exemplary embodiment, process sequence system 1502 includes one or more process lists, such as tote prep processes, prescription fill processes, prescription verification processes, and other suitable processes, and tracks when completion of each process step has occurred so as to prevent a user from changing the status of a process prior to performing all of the process steps. In this exemplary embodiment, a tote prep process can include the steps of scanning or entering a user ID; scanning or entering a tote or receptacle number; entering prescription data; printing a prescription label; scanning the prescription label; capturing an image of a handwritten prescription using a digital camera; and capturing an image of a pharmaceutical with a digital camera if an image is not available. A prescription fill process can include the steps of scanning or entering a user ID; scanning or entering a tote or receptacle number; scanning the prescription label; comparing the prescription label at the prescription fill step to a prescription label at the tote prep step; scanning a drug bottle identifier; comparing the prescription data to the drug bottle data; displaying a stored image of the pharmaceutical; and generating error notifications if an expected match does not occur. A prescription verification process can include the steps of scanning or entering a user ID; scanning or entering a tote or receptacle number; scanning the prescription label; comparing the prescription label to the handwritten prescription; displaying a stored image of the pharmaceutical; and generating error notifications if an expected match does not occur. Process sequence system 1502 can also interface with other suitable systems, such as robotic systems that retrieve bottles of pharmaceuticals from predetermined storage areas and transport them to personnel that are filling prescriptions. Other suitable processes can likewise be performed.

Image upload system 1504 allows image data of a pharmaceutical, a handwritten prescription, a printed label, or other suitable image data to be generated. In one exemplary embodiment, image upload system 1504 includes a camera that provides flexible image data generation capability such that different objects can be imaged. Image upload system 1504 further allows a number of image data sets of an object to be made and reviewed by an operator, so as to allow the operator to quickly select clear image data, or to generate additional image data if needed.

Error tracking system 1506 tracks errors committed by users at tote prep, prescription fill, verification, or other suitable stages. In one exemplary embodiment, error tracking system 1506 can determine the number of times an operator attempted to use the wrong pharmaceutical to fill a prescription, the number of times an operator entered data from a handwritten prescription incorrectly, the number of times that the prescriptions in a tote that the operator previously handled were not present in the tote at the next stage, or other errors that can result in incorrect pharmaceuticals being provided to patients. In this manner, pharmacy workers that commit a larger than acceptable number of errors can be detected.

Workflow management system 1508 tracks pharmacy workload data, such as the length of time a worker requires to perform tote prep, prescription fill, prescription verification, the number of operations performed by a worker, the number of prescriptions per tote handled by the worker, or other suitable functions. Likewise, workflow management system 1508 can display the status of prepared totes that have not had prescriptions filled, the number of filled prescriptions that have not been verified, or other suitable data that can be used to determine whether prescriptions are taking longer than an allotted time to prepare, when a prescription is expected to be ready, or other data of interest.

In operation, system 1500 allows a pharmacy operation having two or more personnel to be managed by tracking the length of time each worker requires to perform predetermined tasks and the error rates for workers. Likewise, pharmacy process data can be generated for each worker, image data required to support and document actions performed by operators of system 1500 can be generated, and other suitable processes can be performed to improve pharmacy management.

Figure 16:
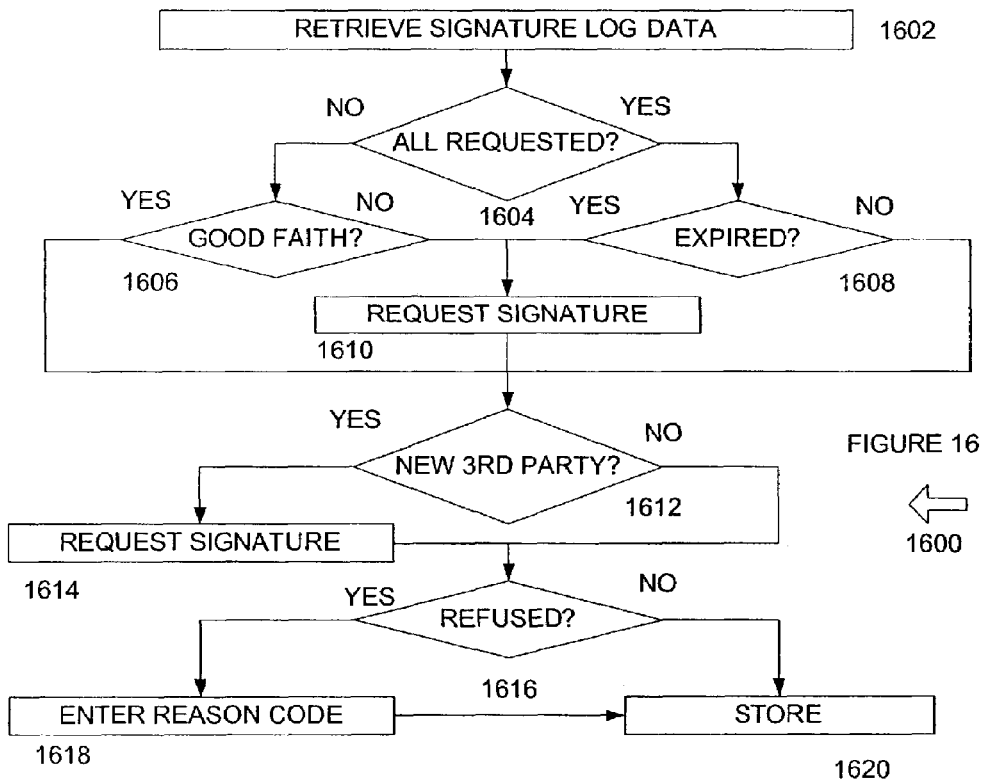
FIG. 16 is a flowchart of a method for signature capture in accordance with an exemplary embodiment of the present invention.

FIG. 16 is a flowchart of a method 1600 for signature capture in accordance with an exemplary embodiment of the present invention. Method 1600 allows patient signatures to be obtained when necessary to support pharmacy operations.

Method 1600 begins at 1602 where signature log data is retrieved, such as when a patient presents a prescription for filling. The method then proceeds to 1604 where it is determined whether all signatures have been obtained for the patient. For example, a signature can be required for acceptance of a privacy policy, for receipt of reminders of prescription refills, for authorizing pick-up of prescriptions by third-parties, or for other purposes where patient data may be disclosed or used for treatment, payment, or health care operations. If all requested signature have been obtained, the method proceeds to 1608. Otherwise, the method proceeds to 1606 where it is determined whether a good faith effort has been made to obtain the patient signatures. In one exemplary embodiment, the number of times that a patient is approached and requested to sign can be set by the pharmacy, for each patient, or in other suitable manners so as to establish that a good faith effort was made to obtain a signature. If the number of times a signature was requested is equal to or greater than the number of times for establishing a good faith effort, the method proceeds to 1612. Otherwise, the method proceeds to 1610 where the signature is requested. In one exemplary embodiment, a palm pilot or other handheld device can be used to requested the signature, such as where the patient is at a pharmacy drive-through window. The method then proceeds to 1612.

If it is determined that all requested signatures have been obtained, the method proceeds to 1608 where it is determined whether any of the signatures have expired. In one exemplary embodiment, signatures for refill reminders or other signatures can be renewed once a year, new privacy policy signatures may need to be obtained if the privacy policy is revised, or other expired signatures may need to be renewed. If no signatures have expired, the method proceeds to 1612. Otherwise, the method proceeds 1610 where the signature is requested.

At 1612, it is determined whether a new signature is required, such as for a third party agreement. If no new signature is required, the method proceeds to 1616, otherwise the method proceeds to 1614 where a signature is requested. The method then proceeds to 1616 where it is determined whether the signature was refused. If the signature was not refused, the method proceeds to 1620 where the signature data is stored. If the signature was refused, the method proceeds to 1618 where a reason code is entered, and the method then proceeds to 1620 where the reason code is stored.

In operation, method 1600 allows signature data to be obtained where needed, so as to replace paper signature logs with electronic databases. Method 1600 further provides reminders where new signatures are required, such as where a signature has expired, a privacy policy has been revised, or where otherwise suitable. Method 1600 further allows the number of times for a good faith attempt to obtain a signature to be set according to the patient, pharmacy, or based on other suitable criteria.

Although the invention has been described with reference to a specific embodiment, these descriptions are not meant to be construed in a limiting sense. Various modifications of the disclosed embodiments, as well as alternative embodiments of the invention will become apparent to persons skilled in the art upon reference to the description of the invention. It is therefore contemplated that the claims will cover any such modifications or embodiments that fall within the true scope and spirit of the invention.

What is claimed is:

1. An apparatus for multi-media data organization and transmission of information relating to the provision of service on-site, the apparatus comprising:
   an on-site computer having a microprocessor, a memory storage, a display for providing information to an on-site service provider, and an input device for receiving information and commands from an on-site service provider;
   a remote computer having a microprocessor and a memory storage;
   a display for providing information to a remote service provider, and an input device for receiving information and commands from a remote service provider;
   an imaging device operatively coupled to said memory storage of said on-site computer for capturing images for storage in said memory storage of said on-site computer;
   a database defined in said memory storage of said on-site computer for storing a plurality of information relating to an event, said database including provision for annotations of said images;
   a database defined in said memory storage of said remote computer for storing a plurality of information relating to an event, said database including provision for annotations of said images;
   a program executable by said on-site computer, said program providing a graphical user interface on said display of said on-site computer, said program having an imaging module with document and image capture filing and scanning functions, said graphical user interface accepting an input from said input device of said on-site computer to control said program;
   a data transmission connection between said on-site computer and said remote computer for transferring data between the memory storage of said on-site computer and the memory storage of said remote computer; and
   a data synchronizer for making the data contents of fields of filed information available to both the on-site service provider and the remote service-provider in, respectively, said database defined in said memory storage of said on-site computer and said database defined in said memory storage of said remote computer the same, the data synchronizer further comprising:
   a sync system determining whether a sync file is present before the data contents of fields of information are transmitted.

2. The apparatus of claim 1 wherein the sync file comprises patient profile data.

3. The apparatus of claim 1 wherein the sync file comprises a patient folder.

4. The apparatus of claim 1 wherein the on-site computer comprises an excerpt transfer system transmitting an excerpt of a data record to a third party.

5. The apparatus of claim 1 further comprising a record encapsulation system encapsulating the data contents of the fields of filed information.

6. The apparatus of claim 4 further comprising a detail encapsulation system encapsulating the excerpt of the data record prior to transmission.

7. The apparatus of claim 1 wherein the remote computer further comprises a record notification system generating notification data after receipt of the fields of filed information from the on-site computer.

8. The apparatus of claim 1 wherein the on-site computer further comprises a record access tracking system determining whether a data record has been accessed and modified.

9. The apparatus of claim 4 wherein the remote computer further comprises:
   a data input system providing additional data to the excerpt of the data record; and
   a detail encapsulation system encapsulating the additional data and the excerpt of the data record.

10. The apparatus of claim 1 wherein said plurality of information is a graphic image in one of a DICOM format or a TIFF format.

11. A method for creating a multimedia record corresponding to the provision of service on-site by an on-site service provider comprising the steps of:
    creating an episode record having a unique identifier by means of service-provider input at an on-site location;
    capturing an image relating to the episode record;
    storing the image in said episode record;

transferring data corresponding to the image to a remote computer if a sync file is present at the remote computer; and displaying the image corresponding to the image data in said remote computer.

12. The method of claim 11 further comprising encapsulating the episode record to prevent the episode record from being modified.

13. The method of claim 12 wherein encapsulating the episode record comprises:

generating a data value based on the data structure of the episode record; and storing the data value for use in determining whether the data structure of the episode record has been altered.

14. The method of claim 11 wherein transferring data corresponding to the image to the remote computer comprises operating the remote computer in unattended mode.

15. The method of claim 11 wherein transferring the data corresponding to the image to the remote computer if the sync file is present at the remote computer further comprises transferring the sync file to the remote computer prior to transferring the data corresponding to the image if the sync file is not present at the remote computer.

16. The method of claim 11 wherein capturing the image relating to the episode record comprises capturing an image of a signature.

17. The method of claim 11 wherein capturing the image relating to the episode record comprises capturing an image of a prescription package.

18. The method of claim 11 further comprising receiving signature data at the remote computer.

19. A system for multi-media data organization and transmission of information relating to the provision of service on-site, the system comprising:

an on-site system receiving information and commands from an on-site service provider;

a remote system having a display for providing information to a remote service provider;

an imaging device for generating image data for storage in the on-site system;

a database defined in the on-site system for storing a data record, the database including provision for annotations of the image data; a database defined in the remote system for storing the data record, the database including provision for annotations of the image data;

a graphical user interface on the on-site system having an imaging module with image capture functions, the graphical user interface accepting an input from the on-site system;

a data transmission connection between the on-site system and the remote system for transferring data between the on-site system and the remote system; and a data synchronizer for making the image data available to both the on-site service provider and the remote service-provider, the data synchronizer further comprising a sync system determining whether a sync file is present before the image data is transmitted.

20. The system of claim 19 further comprising a record encapsulation system encapsulating the data record.

21. The system of claim 19 wherein the remote system further comprises a record notification system generating notification data when the image data has been transferred to the remote system.

22. An apparatus for multi-media data organization and transmission of information relating to the provision of service on-site, the apparatus comprising:

an on-site computer having a microprocessor, a memory storage, a display for providing information to an on-site service provider, and an input device for receiving information and commands from an on-site service provider;

a remote computer having a microprocessor and a memory storage;

a display for providing information to a remote service provider, and an input device for receiving information and commands from a remote service provider;

an imaging device operatively coupled to said memory storage of said on-site computer for capturing images for storage in said memory storage of said on-site computer;

a section of said memory storage of said on-site computer for storing a plurality of information relating to an event;

a section of said memory storage of said remote computer for storing a plurality of information relating to an event;

a program executable by said on-site computer, said program providing a graphical user interface on said display of said on-site computer, said program having an imaging module with document and image capture filing and scanning functions, said graphical user interface accepting an input from said input device of said on-site computer to control said program;

a data transmission connection between said on-site computer and said remote computer for transferring data between the memory storage of said on-site computer and the memory storage of said remote computer; and a data synchronizer for ensuring the data contents of fields of filed information are available to both the on-site service provider and the remote service-provider in, respectively, said section of said memory storage of said on-site computer and said section of said memory storage of said remote computer the same, the data synchronizer further comprising:

a sync system determining whether a sync file is present before the data contents of fields of information are transmitted.

23. The apparatus of claim 22 wherein the sync file comprises patient profile data.

24. The apparatus of claim 22 wherein the sync file comprises a patient folder.

25. The apparatus of claim 22 wherein the on-site computer comprises an excerpt transfer system transmitting an excerpt of a data record to a third party.

26. The apparatus of claim 25 further comprising a detail encapsulation system encapsulating the excerpt of the data record prior to transmission.

27. The apparatus of claim 25 wherein the remote computer further comprises:

a data input system providing additional data to the excerpt of the data record; and a detail encapsulation system encapsulating the additional data and the excerpt of the data record.

28. The apparatus of claim 22 further comprising a record encapsulation system encapsulating the data contents of the fields of filed information.

29. The apparatus of claim 22 wherein the remote computer further comprises a record notification system generating notification data after receipt of the fields of filed information from the on-site computer.

30. The apparatus of claim 22 wherein the on-site computer further comprises a record access tracking system determining whether a data record has been accessed and modified.

31. The apparatus of claim 22 wherein said plurality of information is a graphic image in one of a DICOM format or a TIFF format.

32. A system for multi-media data organization and transmission of information relating to the provision of service on-site, the system comprising:
- an on-site system receiving information and commands from an on-site service provider, the on-site system having an imaging module with image capture functions;
- a remote system having a display for providing information to a remote service provider;
- an imaging device for generating image data for storage in the on-site system;
- a section of memory storage in the on-site system for storing a data record;
- a section of memory storage in the remote system for storing the data record;
- a data transmission connection between the on-site system and the remote system for transferring data between the on-site system and the remote system; and
- a data synchronizer for making the image data available to both the on-site service provider and the remote service-provider, the data synchronizer further comprising a sync system determining whether a sync file is present before the image data is transmitted.

33. The system of claim 32 further comprising a record encapsulation system encapsulating the data record.

34. The system of claim 32 wherein the remote system further comprises a record notification system generating notification data when the image data has been transferred to the remote system.

35. An apparatus for multi-media data organization and transmission of information relating to the provision of service, the apparatus comprising:
- an on-site computer having a microprocessor, a memory storage for storing a first plurality of fields of information relating to an event, a display for providing information to an on-site person, and an input device for receiving information and commands from the on-site person;
- a remote computer having a microprocessor, a memory storage for storing a second plurality of fields of information relating to the event, a display for providing information to a remote person, and an input device for receiving information and commands from the remote person;
- a diagnostic record system operatively coupled to the on-site computer for capturing diagnostic record data for storage in the first plurality of fields of information;
- a program executable by the on-site computer, the program providing a graphical user interface on the display of the on-site computer, the program configured to store data in the first plurality of fields of information, the graphical user interface accepting an input from the input device of the on-site computer to control the program;
- a data transmission connection between the on-site computer and the remote computer for transferring data between the memory storage of the on-site computer and the memory storage of the remote computer; and
- a file transfer system of the on-site computer configured to make the data contents of the first plurality of fields of information in the memory storage of the on-site computer available to the remote person in the second plurality of fields of information in the memory storage of the remote computer.

36. The apparatus of claim 35, wherein the data contents of the first plurality of fields of information comprises patient profile data.

37. The apparatus of claim 35, wherein the data contents of the first plurality of fields of information comprises a patient folder.

38. The apparatus of claim 35, wherein the data contents of the first plurality of fields of information comprises diagnostic record data captured by the diagnostic record system.

39. The apparatus of claim 35, wherein the data contents of the first plurality of fields of information comprises data selected from a group consisting of: systolic blood pressure data, diastolic blood pressure data, pulse rate data, pulse oximetry data, temperature data, bronchial capacity data, bronchial peak flow volume data, spirometry test data, spirometry test type data, blood glucose reading average, blood glucose reading count, height in feet, height in inches, weight in pounds, and electro-cardio gram data.

40. The apparatus of claim 35, wherein the on-site computer comprises an excerpt transfer system configured to transmit an excerpt of the data contents of a field in the first plurality of fields of information to a third party.

41. The apparatus of claim 40, further comprising a detail encapsulation system configured to encapsulate the excerpt of the data contents of the field prior to transmission.

42. The apparatus of claim 40, wherein the remote computer further comprises:
- a data input system configured to provide additional data to the excerpt of the data contents of the field; and
- a detail encapsulation system configured to encapsulate the additional data and the excerpt of the data contents of the field.

43. The apparatus of claim 35, further comprising a record encapsulation system configured to encapsulate the data contents of the first plurality of fields of information.

44. The apparatus of claim 35, wherein the remote computer further comprises a record notification system configured to generate notification data after receipt of the data contents of the first plurality of fields of information by the remote computer.

45. The apparatus of claim 35, wherein the on-site computer further comprises a record access tracking system configured to determine whether a field in the first plurality of fields of information has been accessed and modified.

46. The apparatus of claim 35, wherein the data contents of the first plurality of fields of information comprises one or more graphic images in one of a DICOM format or a TIFF format.

47. The apparatus of claim 35, further comprising a file transfer system of the remote computer configured to make the data contents of the second plurality of fields of information in the memory storage of the remote computer available to the on-site person in the first plurality of fields of information in the memory storage of the on-site computer.

48. The apparatus of claim 35, wherein the diagnostic record system comprises an imaging device and the diagnostic record data comprises one or more images.

49. The apparatus of claim 35, wherein the diagnostic record system comprises a video camera and the diagnostic record data comprises a video feed.

50. A system for multi-media data organization and transmission of information relating to the provision of service, the system comprising:
- an on-site system receiving information and commands from an on-site person, the on-site system having a memory storage storing a first plurality of fields of information relating to an event;

a remote system having a display for providing information to a remote person and a memory storage for storing a second plurality of fields of information relating to the event;

a diagnostic record system for generating diagnostic record data for storage in the first plurality of fields of information;

a data transmission connection between the on-site system and the remote system for transferring data between the on-site system and the remote system; and a file transfer system of the on-site system configured to make the data contents of the first plurality of fields of information in the memory storage of the on-site system available to the remote person in the second plurality of fields of information in the memory storage of the remote system.

51. The system of claim 50, further comprising a record encapsulation system configured to encapsulate the data contents of the first plurality of fields of information.

52. The system of claim 50, wherein the remote system further comprises a record notification system configured to generate notification data when the data contents of the first plurality of fields of information has been transferred to the remote system.

53. The system of claim 50, further comprising a file transfer system of the remote system configured to make the data contents of the second plurality of fields of information in the memory storage of the remote computer available to the on-site person in the first plurality of fields of information in the memory storage of the on-site system.

54. The system of claim 50, wherein the data contents of the first plurality of fields of information comprises data selected from a group consisting of: systolic blood pressure data, diastolic blood pressure data, pulse rate data, pulse oximetry data, temperature data, bronchial capacity data, bronchial peak flow volume data, spirometry test data, spirometry test type data, blood glucose reading average, blood glucose reading count, height in feet, height in inches, weight in pounds, and electro-cardio gram data.

55. The system of claim 50, wherein the diagnostic record system comprises an imaging device and the diagnostic record data comprises one or more images.

56. The system of claim 50, wherein the diagnostic record system comprises a video camera and the diagnostic record data comprises a video feed.

57. The system of claim 50, wherein the event comprises an episode of medical services.

58. The system of claim 50, wherein the event comprises an episode of mechanical analysis.

59. The system of claim 50, wherein the remote system comprises a notification system configured to generate notification data that indicating the data contents of the first plurality of fields of information are available to the remote person.

60. The system of claim 50, wherein the data contents of the first plurality of fields of information comprises data selected from a group consisting of: identification of a patient, identification of the on-site person, identification of the remote person, identification of patient insurance, identification of a pharmacy, identification of the location of the on-site system, identification of the location of the remote system, and identification of an activity.

61. The system of claim 50, wherein the data contents of the first plurality of fields of information comprises data selected from a group consisting of: last menstrual period, gestational age, times pregnant, times given birth, patient abort history, single/multiple fetus, fetal heart activity, fetal extremeties activity, fetal respiration activity, fetal presentation grade, normal amniotic fluid data, hydro amniotic fluid data, oligo amniotic fluid data, variable amniotic fluid data, anterior placenta position, posterior placenta position, fundal placenta position, placenta condition, placenta grade, cranium identification data, spine identification data, post fossa identification data, ventricles identification data, heart 4 chambers identification data, left VOT identification data, right VOT identification data, fluid GI identification data, bladder identification data, right kidney identification data, left kidney identification data, male gender identification data, female gender identification data, 3 vessel cord identification data, umbilicus identification, extremeties identification, face identification, amniotic fluid volume grade, tone grade, reactivity grade, movement grade, respiration grade, sum of bio elements, sum of bio grades, bi-parietal diameter, bi-parietal age, bi-parietal percentile, bi-parietal associated image number, head circumference measurement, head circumference age, head circumference percentile, head circumference associated image number, abdominal circumference measure, abdominal circumference age, abdominal circumference percentile, abdominal circumference associated image number, long femur bone measurement, long femur bone age, long femur bone percentile, long femur bone associated image number, crown/rump length measurement, crown/rump length age, crown/rump length percentile, crown/rump length associated image number, fetal sac measurement, fetal sac age, fetal sac percentile, fetal sac image number, average age, total cardial diameter, total cardial age, total cardial percentile, total cardial image number, humerus length measurement, humerus length age, humerus length percentile, humerus length associated image number, effective fetal weight, estimated date of delivery, fetus systolic blood pressure, and fetus diastolic blood pressure data.

62. The system of claim 50, wherein the data contents of the first plurality of fields of information comprises a blood glucose measurement.

63. The system of claim 50, wherein the data contents of the first plurality of fields of information comprises data selected from a group consisting of: forced vital capacity (FVC), forced expiratory volume (FEV) 0.5 second, forced expiratory volume 1st second, forced expiratory volume 3rd second, percentage ratio of FEV (timed) to FVC, peak expiratory flow rate, forced expiratory flow @ 25%, forced expiratory flow @ 50%, forced expiratory flow @ 75%, forced expiratory flow @ middle of test, forced inspiratory vital capacity, forced inspiratory vital capacity @ 0.5 second, forced inspiratory vital capacity @ 1 second, forced inspiratory vital capacity (FIV) @ 3 second, peak inspiratory flow (FIF) rate, FIF @ 50%, FIF @ 75%, FIF between 200 ml and 1200 ml. 1000 ml measure, percentage ratio of expiratory time to volume, maximum voluntary ventilation, maximum total ventilation, respiratory rate, slow vital capacity, body temperature and pressure, saturated, and room temperature during test.

64. The system of claim 50, wherein the data contents of the first plurality of fields of information comprises historical biometric data.

65. The system of claim 50, further comprising a record server configured to:

receive the data contents of the first plurality of fields of information from the on-site system; and provide the data contents to the remote system.

66. The system of claim 65, wherein the record server is further configured to receive comment data from the remote system and associate the comment data with the data contents.

67. The system of claim 65, wherein the record server is further configured to receive comment data from the on-site system and associate the comment data with the data contents.

68. The system of claim 65, wherein the record server comprises a notification system configured to generate notification data indicating that the data contents have been received.

* * * * *